(12) United States Patent
Kutty

(10) Patent No.: US 10,777,308 B2
(45) Date of Patent: *Sep. 15, 2020

(54) ELECTRONIC HEALTH RECORD SYSTEM AND METHOD

(71) Applicant: Mohan Kutty, Tampa, FL (US)

(72) Inventor: Mohan Kutty, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/296,517

(22) Filed: Mar. 8, 2019

(65) Prior Publication Data

US 2019/0206534 A1 Jul. 4, 2019

Related U.S. Application Data

(63) Continuation of application No. 14/977,824, filed on Dec. 22, 2015, now Pat. No. 10,276,264, which is a
(Continued)

(51) Int. Cl.
| | |
|---|---|
| *G16H 15/00* | (2018.01) |
| *H04L 29/06* | (2006.01) |
| *G06F 19/00* | (2018.01) |
| *G06F 16/9535* | (2019.01) |
| *G16H 40/63* | (2018.01) |
| *G16H 10/60* | (2018.01) |
| *G16H 50/20* | (2018.01) |

(Continued)

(52) U.S. Cl.
CPC ......... *G16H 15/00* (2018.01); *G06F 16/9535* (2019.01); *G06F 19/328* (2013.01); *G06F 19/3456* (2013.01); *G16H 10/60* (2018.01); *G16H 20/10* (2018.01); *G16H 40/20* (2018.01); *G16H 40/63* (2018.01); *G16H 50/20* (2018.01); *H04L 63/10* (2013.01)

(58) Field of Classification Search
CPC ........ G16H 15/00; G16H 10/60; G16H 50/20; G16H 40/63; G06F 17/30867; G06F 19/00; G06F 19/328; G06F 19/3456; H04L 63/10

See application file for complete search history.

(56) References Cited

U.S. PATENT DOCUMENTS

| | | |
|---|---|---|
| 7,593,952 B2 | 9/2009 | Soll |
| 7,899,687 B2 | 3/2011 | Morris |

(Continued)

FOREIGN PATENT DOCUMENTS

| | | |
|---|---|---|
| TW | 424188 | 3/2001 |
| TW | 200509856 | 3/2005 |

(Continued)

OTHER PUBLICATIONS

Office Action issued in Taiwan Patent Application No. 101139178 dated Nov. 27, 2014.

(Continued)

*Primary Examiner* — Linh Giang Le
(74) *Attorney, Agent, or Firm* — Jeffrey S. Melcher; Melcher Patent Law PLLC

(57) ABSTRACT

Provided are a system and method for efficiently creating patient health records with help of expert clinical decision support. The system and method also ensures the doctor's documentation and diagnosis comply with the government healthcare quality measures.

20 Claims, 30 Drawing Sheets

Related U.S. Application Data continuation-in-part of application No. 14/701,568, filed on May 1, 2015, now abandoned, said application No. 14/977,824 is a continuation-in-part of application No. 14/497,469, filed on Sep. 26, 2014, now Pat. No. 9,977,864.

(60) Provisional application No. 62/988,369, filed on May 5, 2014, provisional application No. 62/095,919, filed on Dec. 23, 2014, provisional application No. 61/888,097, filed on Oct. 8, 2013.

(51) Int. Cl.
*G16H 40/20* (2018.01)
*G16H 20/10* (2018.01)

(56) References Cited

U.S. PATENT DOCUMENTS

| | | |
|---|---|---|
| 2003/0033169 A1 | 2/2003 | Dew |
| 2004/0078229 A1 | 4/2004 | Gay |
| 2004/0172294 A1* | 9/2004 | Dahlin ............... G06Q 10/0633 |
| | | 705/2 |
| 2006/0116908 A1 | 6/2006 | Dew |
| 2008/0235057 A1 | 9/2008 | Weidenhaupt |
| 2011/0010195 A1 | 1/2011 | Cohn |
| 2011/0301982 A1* | 12/2011 | Green, Jr. ............... G06Q 10/06 |
| | | 705/3 |
| 2012/0004932 A1 | 1/2012 | Sorkey |
| 2012/0278094 A1* | 11/2012 | Kovacevic ............. G06Q 50/22 |
| | | 705/2 |

FOREIGN PATENT DOCUMENTS

| | | |
|---|---|---|
| WO | 1995/24010 | 9/1995 |
| WO | 2010/057890 | 5/2010 |

OTHER PUBLICATIONS

Schnipper J, et. al., "Smart Forms in an Electronic Medical Record: Documentation-Based Clinical Decision Support to Improve Disease Management," Journal of the American Medical Infomatics Association (JAMIA), Hanley and Belfus, Philadelphia, Pa, US, vol. 15, No. 4, Jul. 1, 2008, pp. 513-523.

International Search Report issued in corresponding PCT/IB2012/055473 dated Dec. 3, 2013, pp. 1-4.

Written Opinion issued in corresponding PCT/IB2012/055473 dated Dec. 3, 2013, pp. 1-8.

BioMedSearch.com, Jan. 2008, Clinical Documentation Systems. Accession No. 174372607. http://www.biomedsearch.com/article/Clinical-documentation-systems-another-link/174372607.html.

U.S. Appl. No. 13/633,989 has similar subject matter and same inventor as the present application.

U.S. Appl. No. 14/497,469 has similar subject matter and same inventor as the present application.

\* cited by examiner

Patient Summary

Name : John Doe  DOB : 12/12/1965  Sex : Male  Race : White  Date of Service: 04-20-2012

Vitals
Temp : 37 C  RR : 35  BP : 140/90  Pulse : 72  Weight : 120 lbs  Height : 175 cms  BMI : 22

Present Diagnosis
Chief Complaints - Coughing up Blood
Symptoms - exposed to someone with tuberculosis, travelled abroad, weight loss
Findings - respiratory rales and shows involvement
Impression -Tuberculosis
Investigations -CBC with differential, ESR, Sputum, Chest X-ray PA & Lateral
Plan & Medication -- Pulmonary Consult

Chronic
1. Diabetes Mellitus
2. Hyperlipidemia

HEDIS Measures
1. Hba1c test performed
2. Date: LDL Screening test performed -before 6 months

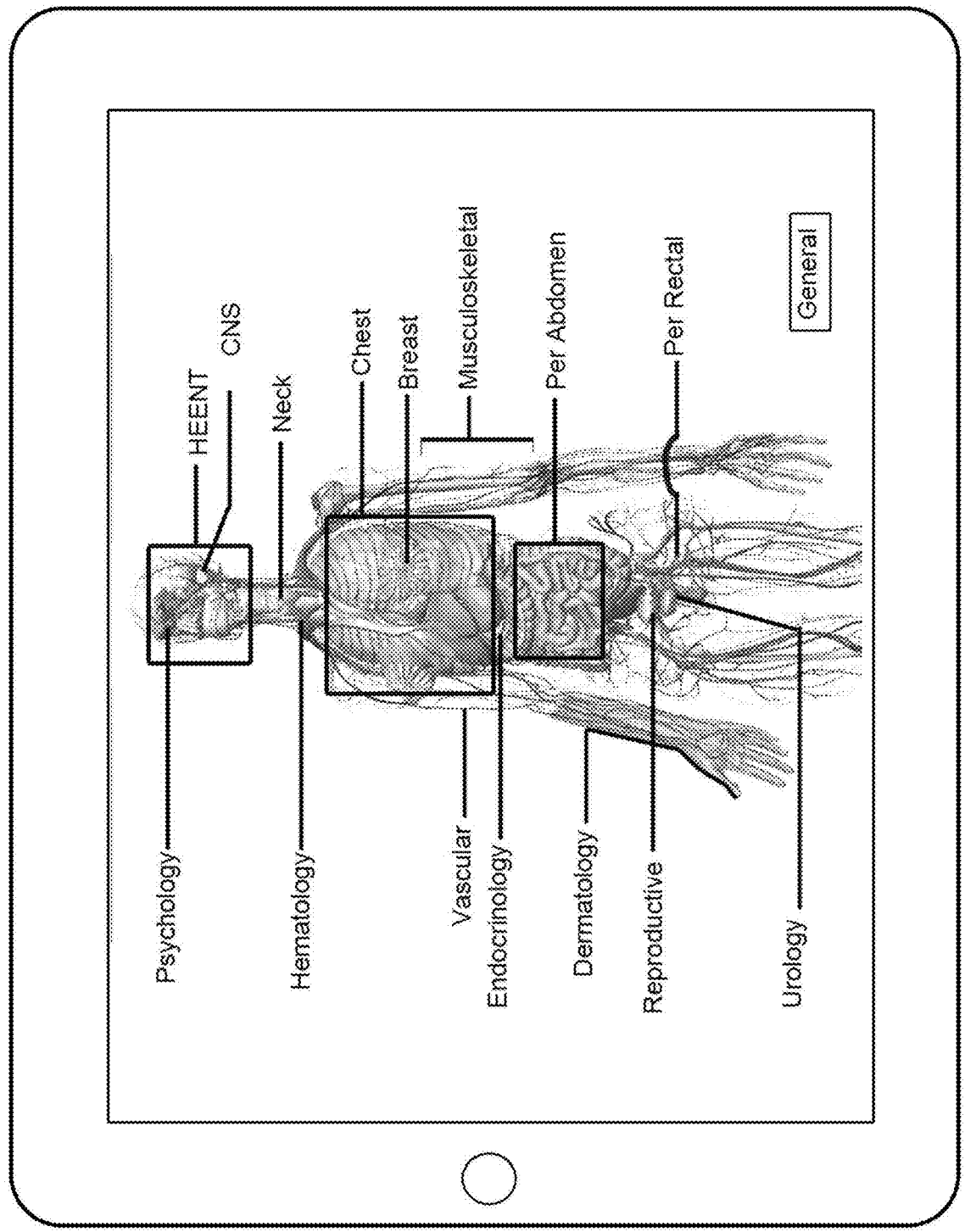

Medications

Mary Doe
DOB: 12-12-1965 | Female

Active | Past

Date of Service: 04-20-2012

Active Medications — 151

Search

| | Name | Dosage | Frequency | Duration | Instruction | Start | |
|---|---|---|---|---|---|---|---|
| + | T. Glucophage (Metformin) | 500 mg | BD | NA | Administer with food | 3-4-2008 | ✱ |
| + | T. Microzide | 12.5 mg | QD | NA | With or without food | 1-9-2011 | R |
| + | T. Tenormin T. (Atenolol) | 50 mg | QD | NA | With or without food | 6-6-2011 | R |
| + | Pyridoxine Hydrochloride | 10mg | QD | NA | Taken with food | 6-6-2011 | R |

152, 153, 154, 155, 156

Delete Pyridoxine Hydrochloride?
Yes | No

ELECTRONIC HEALTH RECORD SYSTEM AND METHOD

FIELD OF THE INVENTION

The invention relates to systems and methods for efficiently creating patient health records with the help of expert clinical decision support. The methods and systems ensure that the doctor's documentation and diagnosis comply with the government healthcare quality measures.

BACKGROUND OF THE INVENTION

There are many conventional electronic health record (EHR) systems. A simple clinical decision support is the simplest form of clinical decision support, which alerts against drug-drug, and drug-allergy prescribing errors. There are EHR systems having quality metrics. For example, in the United States, there are two main quality metrics in use: (1) PQRS (Physicians Quality Reporting System), which is overseen by CMS (the Centre for Medicare and Medicaid Services), and (2) HEDIS (Healthcare Effectiveness Data and Information Set), which is developed by the NCQA (National Committee for Quality Assurance). HEDIS is an initiative by NCQA to develop, collect and standardize measures of health plan performances. The data is reported publicly by NCQA. An EHR system that incorporates these measures can be classified under this category.

For example, a "quality metric" is something like "diabetic patients should have a glycohemoglobin blood test done within the past year (or more often)." An EHR system should be able to present to the clinician an alert in the individual patient record stating "this patient is a diabetic, but has not had a glycohemoglobin done within the past year—he/she is due for one." Alternatively, the EHR system should be able to generate a report, such as a list of all patients (using the same example) who are diabetics but have not had a glycohemoglobin done within the past year.

Diagnosis support EHR systems are complex systems designed to assist doctors in diagnosing the problem. For example, given a patient with "symptom set x" and with "lab test results y," give me the likely diagnoses, and recommended further testing to distinguish between them. Existing decision support systems with diagnosis support are complex and do not fit well with the clinical workflow. Furthermore, these conventional EHR are difficult to use and consume more time to use than paper systems.

CMS has become more stringent in regards to paying for patient health care claims. With this change, it is now required that every patient diagnosis be supported by complete notation of the existing conditions of each patient within the progress notes. Without proper notation in the correct sections of the doctor's notes for any existing diagnosis, CMS views that diagnosis as invalid/unsupported and will not provide funding for that condition. This leaves the doctor and patient with insufficient funds from CMS to pay for their true physical/mental conditions, and therefore, leaving the doctor without the financial means to provide the best care possible for their patients. Without proper documentation, there is insufficient funding to provide proper patient care.

Existing EHR systems are complex and inefficient at the point of care and doctors find it difficult to enter data into these systems. Moreover, documenting patient condition and diagnosis information is usually done after assessing the patient.

The U.S. Government has spent $5 billion and as the estimates approach $28 billion to create an EHR. The present EHR project has been scrapped and rebidding has been started. Pentagon Electronic Health Records Not Ready Until 2017 . . . At least-Defense One, 2/17/14 5-27A.

The British government has spent $16 billion on an EHR for the United Kingdom and the project had to be scrapped. The British authorities concluded that the EHR project had to be built from the bottom up but they have not figured how to go about doing it. Scrapped national EHR program will cost UK Billions, FierceEMR, 2/7/14 5-27A.

SUMMARY OF THE INVENTION

An objective of the invention is to automatically document the diagnosis by integrating diagnosis support to the EHR system.

Another objective of the invention is to provide an EHR system that minimizes errors in coding and delays in submission of claims.

Another objective of the invention is to provide an EHR system that ensures the doctor's documentation and treatment comply with quality metrics set forth by the government.

A further objective of the invention is to provide an EHR system that is efficient and less time consuming than conventional EHR systems.

Another objective of the invention is to provide an EHR system that reduces the chance of an improper diagnosis, missed diagnosis, improper treatment, and/or errors in instructions provided to patients.

Another objective of the invention is to provide an EHR system in which the doctor can enter information during the patient examination.

Another objective of the invention is to reduce prescription errors.

The above objectives and other objectives can be obtained by a method of making a patient health care record comprising;

The above objectives and other objectives can also be obtained by an apparatus for making a patient health care record and invoice comprising:

a cloud based server connected to a network, the cloud based server being in communication with or comprising at least one non-volatile memory, a database stored in the non-volatile memory, the database comprising a patient records database;

a user interface device in communication with the cloud based server via the network;

a chief complaint software module for displaying a list of chief complaints, wherein the chief complaint software module is stored in the non-volatile memory, and the chief complaint software module allows a user to select at least one chief complaint of a patient from among the list of chief complaints;

a symptoms software module for displaying a list of symptoms associated with a selected chief complaint, wherein the symptoms software module is stored in the non-volatile memory, and the symptom software module allows a user to optionally identify each symptom as positive via the user interface device;

a differential diagnosis software module for categorizing possible diagnosis;

a findings software module for displaying a list of possible findings associated with at least one positive symptom or the chief complaint, or a combination of the chief complaint and at least positive symptom, wherein the findings software module is stored in the non-volatile memory;

an impressions software module for displaying a list of possible impressions based on at least one of a positive symptom or a finding, wherein the impressions software module is stored on the non-volatile memory, and the impressions software module allows a user to select a possible impression via the user interface device;

an investigations software module for displaying a list of investigations associated with a possible impression, wherein the investigations software module is stored on the non-volatile memory, and wherein the impressions software module allows a user to confirm or deny a possible impression based on an outcome of an investigation;

a plan and medication module for displaying a treatment associated with a confirmed impression, wherein the plan and medication module is stored on the non-volatile memory;

a query software module for sending a query to the at least one database to retrieve information from the database, the query software constructed for sending a query to the quality metric requirements database including regarding requirements in connection with the at least one selected impression via the user interface device to confirm that the treatment complies with the quality metric and whether additional tests are required to comply with the quality metrics, wherein the query software module is stored on non-volatile memory; and an invoice module for creating a patient health care record and, if an impression is confirmed, an invoice, wherein the invoice and patient health care record are saved to the patient records database.

BRIEF DESCRIPTION OF THE DRAWINGS

FIGS. 3A and 3A1 illustrate an exemplary graphical user interface view of the chief complaints in accordance with the present invention;

FIGS. 3B and 3B1 illustrate an exemplary graphical user interface view of the symptoms a patient can have based on the patient's Chief Complaints in accordance with the present invention;

FIGS. 3C and 3C1 illustrate an exemplary graphical user interface view of the clinical findings in accordance with the present invention;

FIGS. 3D and 3D1 illustrate an exemplary graphical user interface view of the possible impressions based on at least one of a positive symptom or a finding in accordance with the present invention;

FIGS. 3E and 3E1 illustrate an exemplary graphical user interface view of the investigation in accordance with the present invention;

FIGS. 3F and 3F1 illustrate an exemplary graphical user interface view of the plan and medication in accordance with the present invention;

FIG. 3G illustrates an exemplary graphical user interface view of a patient summary in accordance with the present invention;

FIG. 3I illustrates an exemplary graphical user interface view of the clinical findings in pictorial representation in accordance with the present invention;

FIGS. 4A and 4B illustrate an exemplary graphical user interface view of the chronic section in accordance with the present invention;

FIG. 6 illustrates an exemplary graphical user interface of a representative human body showing selectable body systems;

FIGS. 7A-7B illustrate the deactivate and activate features of the EHR system;

FIGS. 8A-8B illustrates exemplary graphical user interfaces of patient medication lists;

FIG. 9A illustrates an exemplary graphical user interface of a chief complaint;

FIG. 9B illustrates an exemplary graphical user interface of a differential diagnosis; and FIG. 9C illustrates an exemplary graphical user interface of screening questions.

DETAILED DESCRIPTION OF THE SYSTEM

In the following description, for purposes of explanation and not limitation, specific details are set forth, such as particular networks, communication systems, computers, terminals, devices, components, techniques, data and network protocols, software products and systems, operating systems, development interfaces, hardware, etc. in order to provide a thorough understanding of the present invention.

However, it will be apparent to one skilled in the art that the present invention can be practiced in other embodiments that depart from these specific details. Detailed descriptions of well-known networks, communication systems, computers, terminals, devices, components, techniques, data and network protocols, software products and systems, operating systems, development interfaces, and hardware are omitted so as not to obscure the description.

The EHR system will now be explained with reference to the attached non-limiting Figures. The operations described in FIGS. and herein can be implemented as executable code stored on a computer or machine readable non-transitory tangible storage medium (e.g., floppy disk, hard disk, ROM, EEPROM, nonvolatile RAM, CD-ROM, etc.) that are completed based on execution of the code by a processor circuit implemented using one or more integrated circuits; the operations described herein also can be implemented as executable logic that is encoded in one or more non-transitory tangible media for execution (e.g., programmable logic arrays or devices, field programmable gate arrays, programmable array logic, application specific integrated circuits, etc.).

Figure 1:
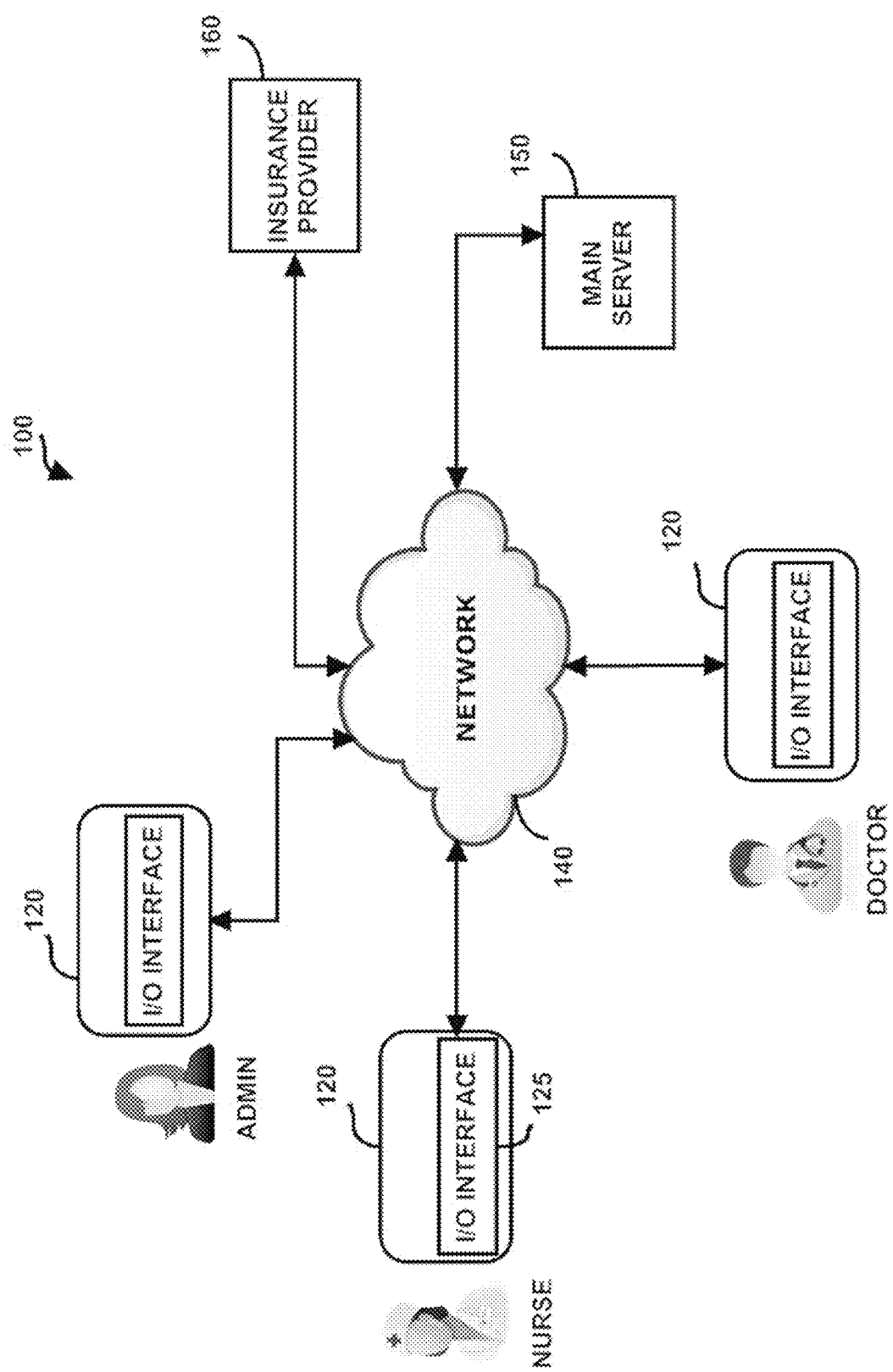
FIG. 1 illustrates a perspective view of the components of an EHR system in accordance with the present invention.

FIG. 1 describes an EHR system 100 for making a patient health care record and CMS compliant invoice. The system 100 comprises a plurality of user interface devices 120 and a main server 150 interconnected via a communication network 140. A component of the system 100 is connected to an external Insurance Provider 160. The system 100 can be set up in a hospital, clinic or similar setting. The user, for example a receptionist, doctor, nurse, or other personnel, or the patient, communicates with the system 100 using the user interface device 120.

Various networks 140 may be implemented in accordance with embodiments of the invention, including a wired or wireless local area network (LAN) and a wide area network (WAN), wireless personal area network (PAN) and other types of networks. When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Computers may be connected over the Internet, an Intranet, Extranet, Ethernet, or any other system that provides communications. Some suitable communications protocols may include TCP/IP, UDP, OSI, Ethernet, WAP, IEEE 802.11, Bluetooth, Zigbee, IrDa or any other desired protocol. Furthermore, components of the system may communicate through a combination of wired or wireless paths.

The EHR system can be accessed via any user interface device 120 that is capable of connecting to the main server 150. The user interface device 120 comprises a display, and preferably a touch screen display. The user interface device 120 also preferably comprises a camera for taking pictures and/or video of patients. The user interface device 120 also preferably includes a microphone for inputting sound, such as verbal commands. In this manner, the doctor can use a speech to text program on the user interface device 120 to enter information by verbal commands.

An exemplary user interface device 120 contains a web browser or similar program, allowing in some embodiments for a secure SSL connection, and able to display HTML and CSS. This includes user interface devices 120 such as tablets, iPads, Mac OS computers, Windows computers, e-readers, and mobile user devices such as the iPhone, Android, and Windows Phone. Preferably, the user interface device 120 is a tablet. The user interface devices 120, preferably support the ability to play video. The user interface devices 120 can connect to the server via the internet and/or wirelessly, such as through a mobile telephone network 140, and/or any other suitable medium. User interface devices 120 are preferably able to communicate to the main server 150 so that content can be started on one user interface device 120 and later continued on a separate user interface device 120. The user interface device 120 preferably includes an I/O interface 125 that allows a user to interact with the system 100. The I/O interface 125 may include any hardware, software, or combination of hardware and software.

Figure 5:
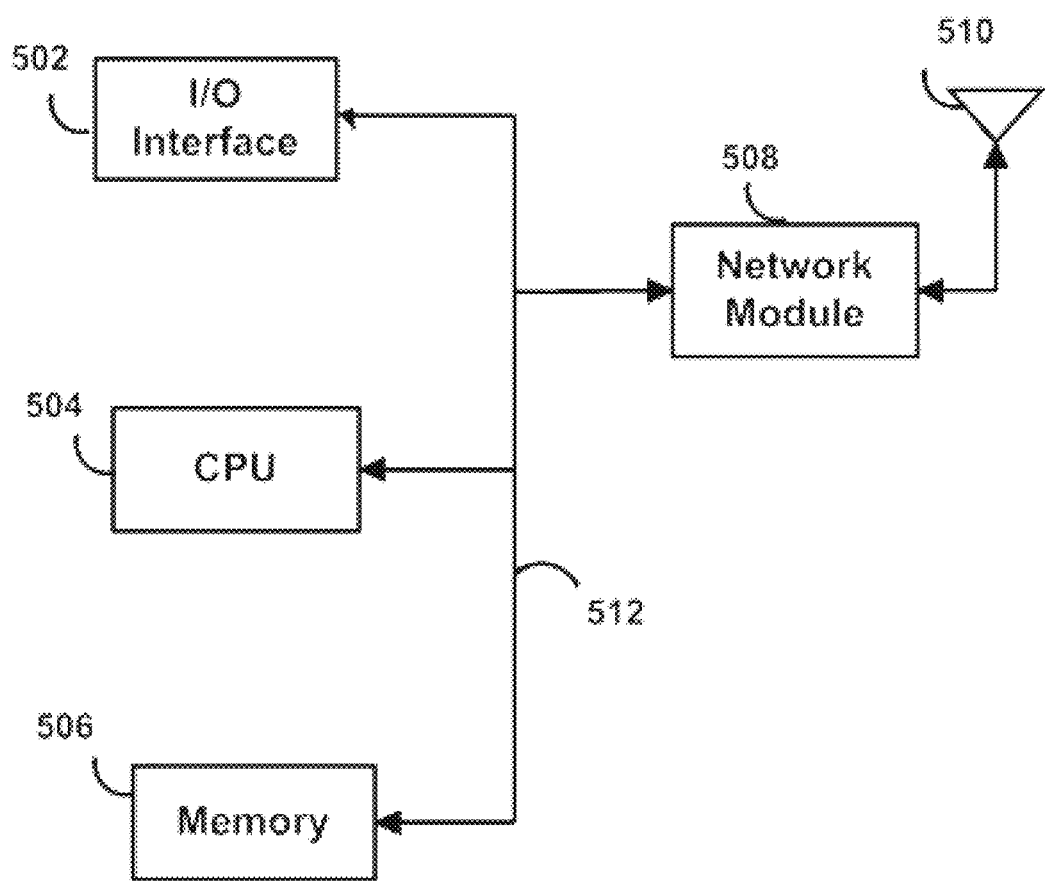
FIG. 5 illustrates a functional block diagram illustrating an exemplary mobile user interface device 120.

Referring to FIG. 5, exemplary CPU 504 of the user interface device 120 can be implemented as a conventional microprocessor, application specific integrated circuit (ASIC), digital signal processor (DSP), programmable gate array (PGA), or the like. The CPU 504 executes the instructions that are stored in order to process data. The set of instructions may include various instructions that perform a particular task or tasks, such as those shown in the appended flowcharts. Such a set of instructions for performing a particular task may be characterized as a program, software program, software, engine, module, component, mechanism, or tool. The memory 506 may include random access memory (RAM), ready-only memory (ROM), programmable memory, flash memory, and the like. The memory 506 include application programs, OS, application data etc. The exemplary computing device 120 also includes a network module 510 connected to an antenna 512 to communicate with rest of the system 100.

A preferred user interface device 120 is an Apple iPad or similar competing touch screen tablet. The doctor can also add notes by typing in the words or using speech recognition software. Pictures and/or videos of the affected areas can be taken by the user interface device 120 and uploaded to a patient records database.

The user interface device 120 is preferably capable of determining the size of features on the human body, such as ulcers, lesions, or moles, when a picture or video is taken. In this manner, a picture or video of the patient can be taken and the features on the patient's body can sized and dated, so that any variations in size of the features can be determined when the pictures or video are taken at different dates. This size information can be stored in the non-transitory tangible memory (e.g., floppy disk, hard disk, ROM, EEPROM, nonvolatile RAM, CD-ROM, etc.) of the server 150. The size of the features can be determined in any desired manner. For example, a scale can be placed on the patient's body so that the user interface device 120 can compare the features to the measured to the scale to determine the size of the features. In another example, the user interface device 120 can have a proximity sensor or GPS to determine the distance of the user interface device 120 to the patient's body, and then the size of the features can be calculated using well known algorithms. The software can be configured to provide commercially available user interface devices 120 with the capability to determine the size of features. Alternatively, a user interface device 120 can be produced having a proximity sensor or gps and camera. The sizes and/or change in size over time can be entered into the EHR using uniform answers.

The main server 150 described herein can include one or more computer systems directly connected to one another and/or connected over the network 140. Each computer system includes a processor, non-transitory tangible memory, user input and user output mechanisms, a network interface, and executable program code (software) comprising computer executable instructions stored in non-transitory tangible memory that executes to control the operation of the main server 150. Similarly, the processors functional components formed of one or more modules of program code executing on one or more computers. Various commercially available computer systems and operating system software can be used to implement the hardware and software. The components of each server can be co-located or distributed. In addition, all or portions of the same software and/or hardware can be used to implement two or more of the functional servers (or processors) shown. The main server 150 can run any desired operating system, such as Windows, Mac OS X, Solaris or any other server based operating systems. Other embodiments can include different functional components. In addition, the present invention is not limited to a particular environment or main server 150 configuration. Preferably, the main server 150 is a cloud based computer system.

The main server 150 preferably includes a web server and the query processing unit. The web server receives the user requests and sends it to the query processing unit. The query processing unit processes the request and responds back to the user interface device 120 via the web server. The query processing unit fetches data from the database server if additional information is needed for processing the request.

A database is stored in the non-transitory tangible memory. The term "database" includes a single database and a plurality of separate databases. The main server 150 can comprise the non-transitory tangible memory or the main server 150 can be in communication with the non-transitory tangible memory storing the database. The database can be stored at different locations. The database can comprise a clinical decision support database, an updatable quality metric requirements database, a patient records database, drug interaction database, and any other desired information stored in non-transitory tangible memory. Examples of other desired information stored in the database includes health requirements from governments other than the U.S, health requirements established by insurance companies, employers, or other groups, and/or requirements provided by drug or medical device companies. If desired, the databases can be organized as a collection of tables. Examples of main tables for the present EHR system include:

1. Clinical decision support table containing the chief complaints and its associated symptoms, findings, impressions, investigations, and treatment plans.
2. Quality metrics requirements table.
3. Patient records table.

The main server 150 can include a plurality of individual computer systems directly connected and/or connected over network 140. Software program modules and data stored in the non-transitory tangible memory the main server 150 may be arranged in logical collections of related information on a plurality of computer systems having associated non-transitory tangible memories. The software and data may be stored using any data structures known in the art including files, arrays, linked lists, relational database tables and the like.

In a preferred system, the main server 150 is maintained at a secure location, such as a US Health Insurance Portability and Accountability Act (HIPAA) compliant data center with access to the internet.

The system 100 can send and receive data from any desire entity, such as labs, radiology departments, pharmacy, speciality hospitals and health insurance companies. Health information exchange to these disparate systems can be achieved using, for example, the HL7 standard.

Basically, the prior art approach has been like trying to solve a jigsaw puzzle without a picture. Complex problems usually have simple solutions. For example, the solution disclosed herein is akin to moving a brick building to distant places. The solution is to identify each brick, such as by numbering, moving the numbered bricks to the new location, and reassembling the building at the new site according to the numbers.

The present invention involves using the thousands of healthcare codes as the numbered building blocks of the EHR. The EHR disclosed herein is based on building up each unique code individually so that medical data can be categorized, stored, retrieved, or manipulated in any manner in relation to each unique code. At the present time there are approximately 19,000 codes in ICD-9, 68,000 codes in ICD-10, and 300,000 codes in SNOMED. New unique codes can be added at any time.

For each code, there can be associated check lists of required questions. Not all codes have required questions. Preferably, all required questions must be answered before the EHR information will be stored in the patient record. The required questions can only be answered by selection of uniform answers from a list of uniform answers, such as by clicking on an icon associated with the desired uniform answer. No written text can be used to answer the required questions so that all possible answers are uniform among all users of the EHR. Written doctor notes, pictures, and other information can be added to the patient file, categorized according to codes, and accessed, but cannot be used to confirm or deny codes. Only answers to the required questions can be used to confirm or deny codes.

The various stages of the doctor's examination of the patient can be classified as desired. Preferred classifications are Chief Complaints, Symptoms, Findings, Impressions, Investigations, and Plan/Medications. The EHR system can include the medical system disclosed in my previously filed international patent application serial No. WO/2013/061192, published on 5 Feb. 2014, the complete disclosure of which is incorporated herein by reference. The system disclosed therein can be used to help the doctor avoid missing a diagnosis and provide medical alerts.

Figure 2A:
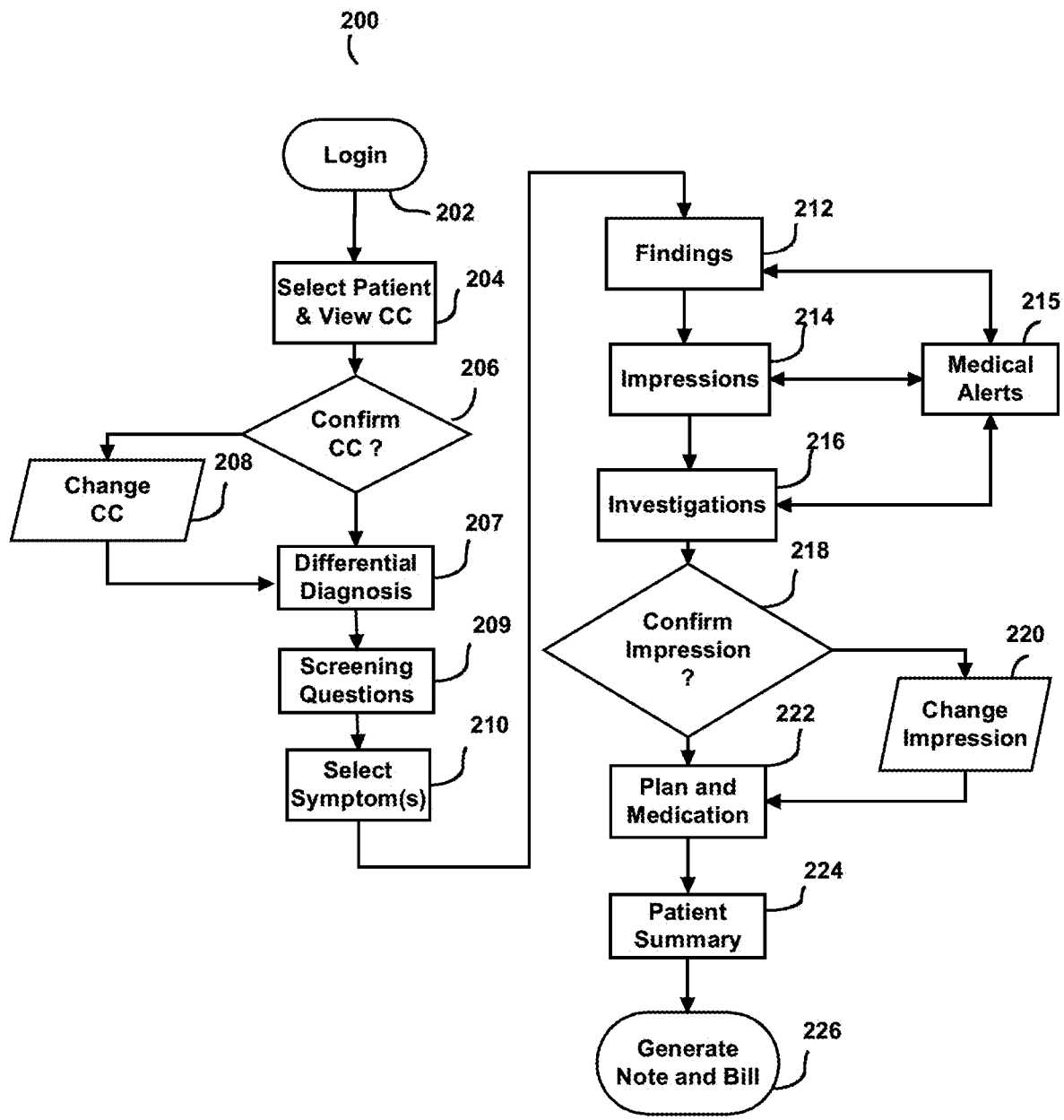
FIG. 2A is a flow diagram for the acute flow for the present invention.
Figure 2B:
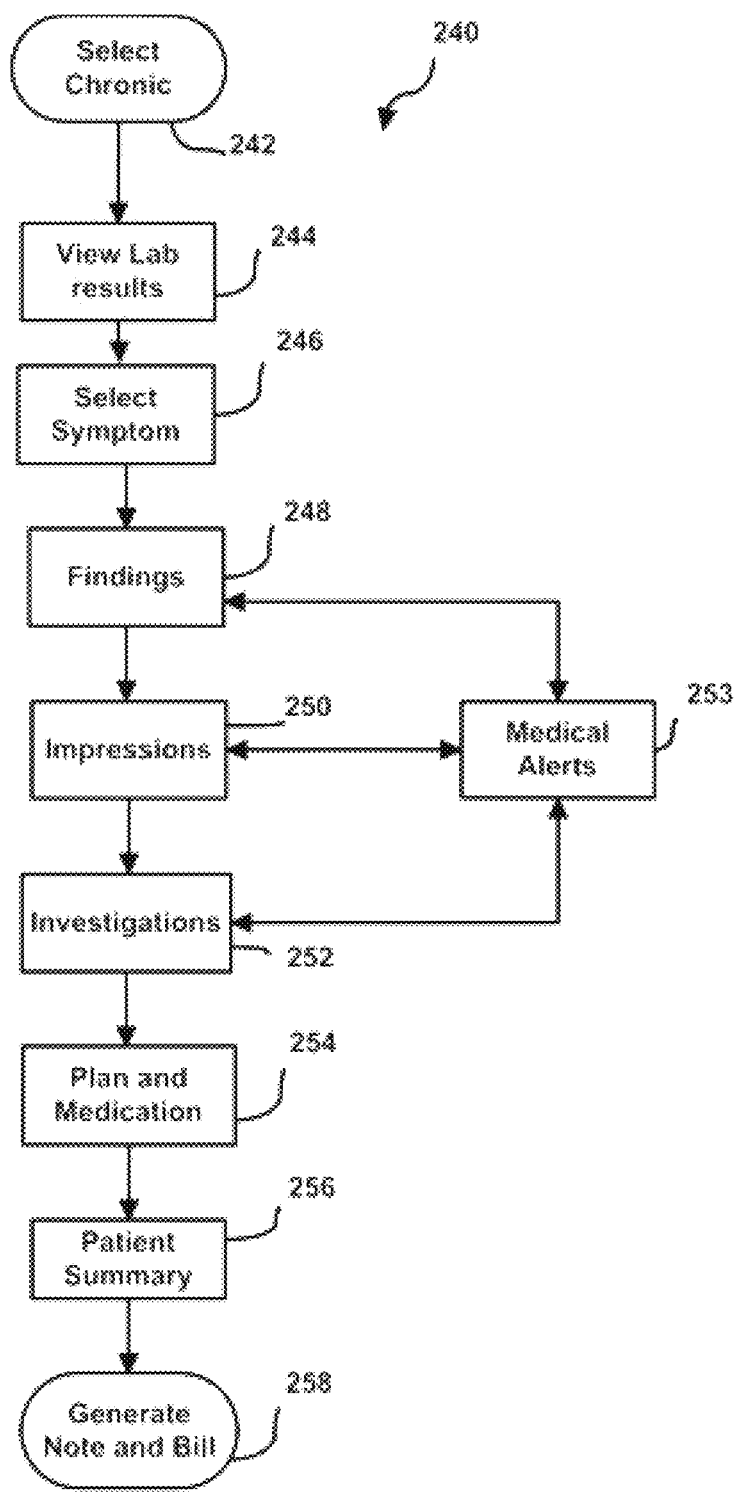
FIG. 2B is a flow diagram for the chronic flow for the present invention.
Figure 2C:
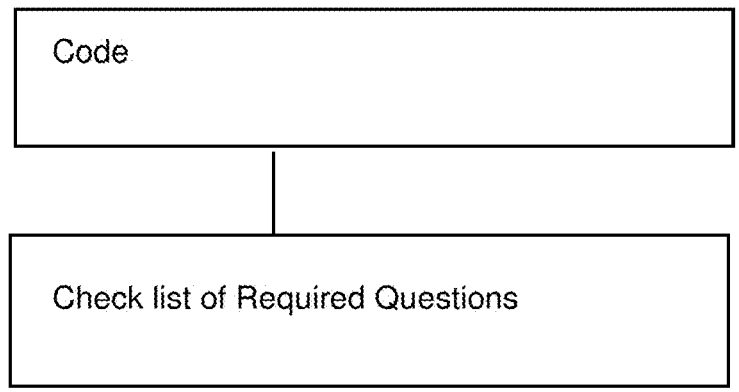
FIG. 2C is a flow diagram for the codes and required questions.

FIGS. 2A-2C illustrate a flow chart of an example of the invention. The present invention involves using the thousands of healthcare codes 201 as the building blocks of the EHR. The EHR disclosed herein is based on building up each unique code 201 individually so that medical data can be categorized, stored, retrieved, or manipulated in any manner in relation to each unique code 201. At the present time there are approximately 19,000 codes in ICD-9, 68,000 codes in ICD-10, and 300,000 codes in SNOMED. New unique codes can be added at any time. The codes 201 can be stored in the memory of the main server 150. The codes 201 are generally classifications including but not limited to diseases, health, problems, conditions, diagnosis, disorders, diseases, complications, impressions, medical procedures, and treatments.

For each code 201, there can be associated check lists of required questions 203, that can be stored in the memory of the main server 150. Not all codes have required questions 203. Preferably, all required questions 203 must be answered before the patient EHR information will be stored in the memory. The required questions 203 can only be answered by selection of uniform answers from a list of uniform answers, such as by clicking on an icon associated with the desired uniform answer. No written text can be used to answer the required questions 203 so that all possible answers are uniform among all users of the EHR. Written doctor notes, pictures, and other information can be added to the patient file and accessed, but cannot be used to confirm or deny codes.

After initial code(s) 201 and the associated required questions 203 are answered for a patient (i.e. the first time the patient EHR file is being made), each successive person accessing the patient EHR file will be required to answer any new check list of required questions 203 caused by a new code 201 being associated with the patient. In addition, the answers to previously required questions 203 can be changed, for example after further patient review, medical tests, and/or medical procedures. Answers to the required questions 203 can result in new codes 201 and their associated required questions 203 being raised and/or present codes 201 and their associated required questions 203 being deleted.

At each level of the patient examination, each time the patient EHR file is changed, any new required questions 203 raised by new codes 201 must be answered. For example, the practitioner entering the initial patient information can enter at least one chief complaint 204, as discussed below. The chief complaint 204 includes the initial symptoms complained of by the patient. Each chief complaint 204 will have a unique codes 201 associated therewith. The unique code 201 can have an associated check list of required questions 203 that must be answered. The required questions 203 can include icons for selecting answers, such as regarding whether certain symptoms are present or not present. The required questions 203 can relate to specific body systems to rule out or confirm a diagnosis.

As the required questions 203 are answered, new codes 201 may be presented and/or present codes 201 deleted. As new codes 201 are presented, new required questions 203 can be presented.

The doctor examining the patient can enter a new chief complaint, delete a chief complain, and/or enter new information such as diagnosis, impression, investigation, and/or treatment plans as desired by selection of related icons, for example as discussed herein below. The doctor's selections may or may not result in new codes 201 associated with the patient and their associated required questions 203 and may also result in deletion of present codes 201 and their associated required questions 203. The doctor must answer the associated required questions 203 if the required questions are new. The doctor can make changes to previously answered required questions 203. Each medical practitioner examining and/or performing a procedure on the patient can enter information into the EHR patent file. Only uniform answers to the required questions 203 can be used to confirm or deny a code.

FIG. 2A illustrates a method 200 performed by the EHR system 100 (illustrated in FIG. 1). The method 200 receives input from the doctor user through the user interface device 120 throughout the doctor's examination of the patient.

The patient fixes an appointment with the receptionist usually over the telephone. The patient is entered into the patient records database stored in a non-transitory tangible memory on the main server 150.

In the first block 202, the main server 150 authenticates the doctor user's login credentials. The doctor selects one entry from the list of patients to be examined for the day in block 204.

If the visit is the patient's first time, the patient or office personnel can enter the patient's personal information into the patient record database using user interface device 120, such as name, address, age, health insurance, and any other information. Alternatively, the patient can have their personal information, and other information, such as medical history, on a memory media, such as an RFID card, flash memory, USB device, hard drive, disc, or other memory device, transferred to the patient records database. The patient's information can also be downloaded over the network 140 from another memory connected to the network 140.

The nurse, or other user, can conduct the initial patient examination and enter the patient's vitals (weight, height etc) into a patient chart in patient record database using the user interface device 120. The values of vital signs can be highlighted on the display of the user interface device 120, such as if any value is outside of the normal range. The highlighting can be any desired color.

The patient can present at least one Chief Complaint (CC) to the doctor or doctor's personnel, such as a nurse, all referred to as "users". The user then selects the patient's chief complaint(s) from a chief complaints list 204, and unique codes 201 and related required questions 203 are displayed. For example, the nurse saves the patient chart and requests the doctor to examine the patient.

Chief complaints 204 are the patient's initial comments to a doctor or nurse describing a symptom. For example, a patient may come to the clinic complaining of chest pain. The chief complaint is the initial input to the user display device 120 for starting the patient examination. The EHR system retrieves from the clinical decision support database the relevant information related to the reported chief complaint, which includes one or more codes 201 and associated required questions 203. The chief complaints can also be referred to as the "Presenting Symptom" by the patient.

For example, a patient may initially complain of one chief complaint, at the beginning of the physical examination. The doctor can use the user interface device 120 to enter the chief complaint 204, for example by tapping the touchscreen. The EHR system will query clinical decision support database for the "associated symptoms" for establishing an identity of an illness, which can be presented as required questions 203. When a patient complaints chest pain as the chief complaint, the EHR system will display any associated symptoms in form of required questions 203 on the user interface device so the doctor can question the patient whether they have any of the symptoms associated with chest pain, such as coughing, palpitations, shortness of breath, etc. The EHR system retrieves the required questions 203 relating to "associated symptoms" from the clinical decision support database for the selected chief complaint. The doctor answers the required questions 203 by selecting answers presented on the screen, so that uniform answers are provided. No text can be entered to answer the required questions 203.

Chief complaints can be categorized as desired by text lists or visually in the EHR system 100. If the chief complaints are categorized in text lists, the user can select chest pain from a written list of chief complaints.

Alternatively, as shown in FIG. 6, the chief complaints can be categorized into plurality of body systems, such as 16 systems. For example, a representative picture of the human body can be shown on the screen showing the different body systems. If the chief complaint is chest pain, the user can touch the body system associated with chest pain on the touch screen, which will then display a list of chief complaints. An exemplary list of 16 general body systems is as follows:

1. General
2. HEENT
3. Neck
4. Chest
5. Breast
6. Per Abdomen
7. Per Rectal
8. Reproductive
9. Urology
10. Musculo-Skeletal
11. Dermatology
12. Vascular
13. Endocrinology
14. Central Nervous System
15. Psychology
16. Hematology The general body systems can be divided into any group as desired.

The doctor can proceed with the same selected chief complaint or change the chief complaint, such as in a decision block 206, if desired. If the decision in the decision block 206 is "YES", the doctor proceeds to the next stage with the current selection. When the decision in the decision block 206 is "NO", the doctor can change the chief complaint in block 208, which will result in a different code 201 and related questions 203.

Often the number of possible associated symptoms or other questions is too large and would require an undesirable amount of time for the user to go through. In such a case, a list of possible diagnosis for a selected chief complaint can be displayed as a differential diagnosis 207 by the system, for example, in the left side of the screen immediately after the chief complaint screen. The differential diagnosis 207 can be categorized as desired. Preferably the differential diagnosis 207 are categorized as common, occasional and rare. Each differential diagnosis 207 has a code 201 and can have related questions 203. If one or more of the categories are selected by the user, only the symptoms associated with the selected category of possible diagnosis can be displayed in the form of required questions 203, which often greatly reduces the number of symptoms listed by the display. The number of possible symptoms can be reduced by selecting the desired possible diagnosis from the differential diagnosis 207, in which case only the possible symptoms associated with the selected possible diagnosis are displayed. The user can add/delete any possible diagnosis from the system's selection at any time. The system also alerts the user of critical symptoms or conditions for the particular chief complaint. User preferences can be made to hide unwanted categories, such as rare, from being displayed.

To reduce the number of possible diagnosis in the differential diagnosis 207, the system can provide the user a set of screening questions 209 (which can also be required questions 203). As the screening questions 209 are answered, the system can remove unlikely possible diagnosis and/or select the possible diagnosis from the differential diagnosis 207. The screening questions can result in a reduced number of possible diagnosis in the differential diagnosis 207, which reduces the number of possible diagnosis.

In an embodiment, the screening questions can relate to specific body systems. As specific body systems are ruled-out, any possible diagnosis associated with the ruled-out specific body system are removed from the differential diagnosis list. In another embodiment, the screening questions can further define the chief complaint. As the chief complaint is further defined, the number of possible diagnosis can be reduced.

For example, selecting as a chief complaint "chest pain", the differential diagnosis 207 can be for example:
 a) Angina;
 b) Myocardial infarction;
 c) GERD; and
 d) Pulmonary embolus.

The differential diagnosis can be categorized on the display with a) and b) being "common," c) as "occasional" and d) as being "rare." Medical alerts, described below, can also be identified on this screen. The chief complaint "chest pain" can be related to the following specific systems:
 i) cardiovascular;
 ii) respiratory;
 iii) gastrointenstinal; or
 iv) musculo/skeletal.

The following exemplary possible screening questions can be listed:
 1) Pressure like heaviness, squeezing or crushing pain;
 2) Related to exertion and relieved with rest or NTG;
 3) Pain radiates to arms, jaw, neck and left or right shoulder;
 4) Heartburn worse at night relieved with antacids;
 5) Trouble swallowing or pain during swallowing;
 6) Pain on taking a deep breath;
 7) Shortness of breath, sweating, hypotension; and
 8) Swelling of leg.

Depending on how these screening questions are answered, certain specific body systems can be ruled out. The ruled-out specific body systems can reduce the number of possible diagnosis in the differential diagnosis.

The system 100 advances to block 210, where a list of possible symptoms are displayed that are associated with the selected chief complaint 206 or with the differential diagnosis 209. The doctor reviews the displayed symptoms (which can be in the form of required questions 203) and answers each required question 203 whether the patient has the symptom, positive, or the patient does not have the symptom, negative. If a symptom present in the patient is not present in the list displayed, the doctor can select other and will be presented with a screen where the additional symptom can be entered by the doctor, such as either by typing or speech recognition software, or selecting a displayed additional symptom from a list, however this text entry cannot be used to confirm or deny a code.

The doctor is presented with a findings screen in block 212 with the associated possible findings for the positive symptoms selected in block 210. Each possible finding can have a code 201 and associated questions 203. The possible findings can also be based on the chief complaint entered into the system. For example, if there are no positive symptoms uncovered during examination, then the doctor can skip the symptoms screen and go to the findings screen, and the findings screen can be based on the chief complaint. When both the chief complaint and positive symptoms are entered, the system can prioritize the most relevant possible findings based on a combination of the chief complaint and positive symptoms selected, i.e. how required questions 203 were previously answered. Findings can be something measured or observed by a doctor, for example during the patient examination that provides evidence. Findings can have no meaning to the patient, and can even go unnoticed. Findings may be meaningful and significant to the doctor in assisting the diagnosis responsible for the patient's symptoms. Findings can be distinguished from symptoms as follows. Both findings and symptoms are something abnormal, relevant to a potential medical condition (confirmed diagnosis), but a symptom is experienced and reported by the patient, while a finding is discovered by the doctor during examination.

The system 100, displays a list of possible impressions, each having a code 201 and possible related required questions 203, based on the entered symptoms and/or findings and prompts the doctor to select an Impression in block 214. The doctor can select an impression by answering the required questions 203 based on a finding or positive symptom.

Impressions include information such as the doctor's suspected diagnosis, confirmed diagnosis, a condition, assessment of a condition, a possible cause (possible diagnosis) of the chief complaint, and/or positive symptom, all of which information can each have a code 201. Impressions can be based on a positive symptom and/or a clinical finding. Possible impressions in the form of required questions 203 are preferably selected based on the chief complaint, positive symptoms and/or clinical findings. Impressions can be diseases, ailments, injuries, etc.

The term condition is used broadly in the medical community to mean a symptom and a chief complaint when the chief complaint is a symptom. The medical community also uses the word condition to refer to a disease or other ailment, i.e. a diagnosis. Each condition can have a code 201.

Medical alerts, shown in block 215, can be generated by the system 100 at any time during the examination and displayed on the user interface device 120. Medical alerts 215 can include, for example, common and rare impressions in which delay in diagnosis would cause permanent disability or death. Preferably, the medical alerts are based on symptoms, findings or impressions, as shown in FIG. 2A. Medical alerts can be in form of required questions 203.

Preferably, the medical alerts overrides the Doctor's selection of the most likely impressions in the alternative embodiment, so that impressions based on medical alerts are not removed from the screen without further input from the Doctor, such as specifically deselecting the medical alert.

The EHR system 100, advances to block 216, and prompts the doctor to select lab investigations to verify the impression, if any are required. Examples of lab investigations include blood tests, X-ray, MRI, EKG, or any other desired test procedure. The lab investigations can each have a code 201.

The investigation can also be used to confirm or deny a condition, by answering required questions 203. For example if a selected possible impression has multiple possible conditions, the possible conditions can be confirmed or denied using the investigation and answering the required questions 203.

After the investigations are over, the patient comes to the doctor with the lab/test results. The doctor verifies in decision block 218 the results with the impression selected in block 214, i.e. the doctor answers any required questions 203. If the decision in the decision block 218 is "YES", the doctor proceeds to the planning and medication in block 222. When the decision in the decision block 218 is "NO", the doctor can change the impression in block 220 before proceeding to block 222.

The planning and medication 222 includes treatment suggested for the patient's confirmed impression (which can also be a confirmed diagnosis or a condition). Based on the information from previous steps, the doctor formulates a plan that may include specialist consultation, drug prescription, diet, exercise, or any other desired treatment. The treatment can have a code 201.

Figure 8B:
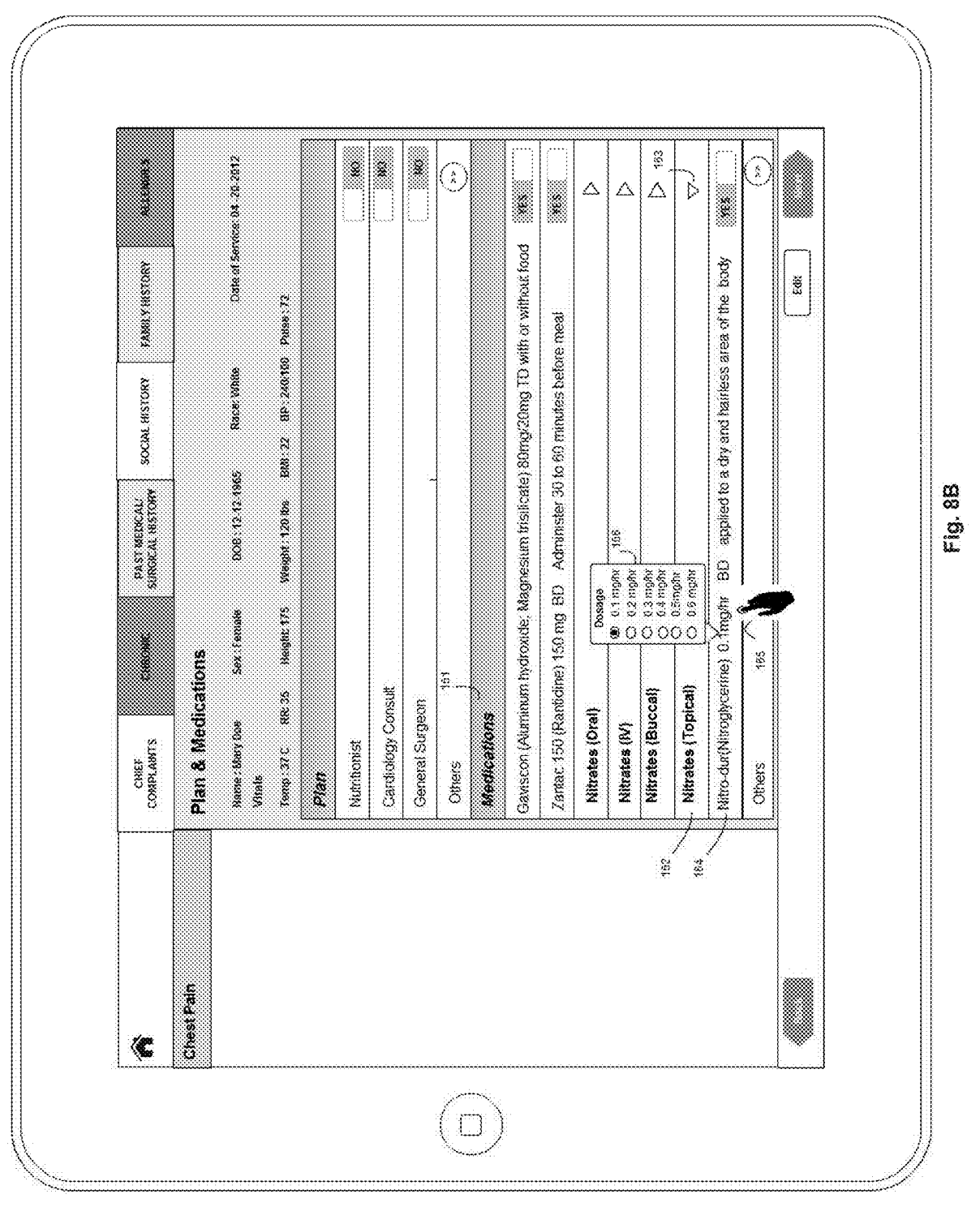

The patient's medications can easily be monitored and changed as desired using the system without typing in any numbers or text. In this manner, prescription errors can be greatly reduced. FIG. 8B shows the selection of drugs during the plan and medication stage 222. The medications 161 are organized into drug classifications 162. When using a touch screen, the doctor can view the various drugs under the classification by taping the expand button 163. While prescribing medication, the doctor orders a drug 164 by selecting from the available drug list, i.e. tapping the appropriate button on the screen. The dosage, frequency, route of administration and comments for the drug 164 is also entered by tapping buttons from the options list 166. A possible drug-drug interaction with the existing medications can be alerted during selections. In addition, drug recommendations specific to race, gender, age or other factor can be displayed. Present and past prescriptions can be viewed on the screen as desired. The selections can be answers to required question 203.

For example, when using a touch screen, if the doctor wants to change a present drug, the change button can be tapped. Alternative drugs will be displayed. The doctor then taps the desired alternative drug. Optional doses will be displayed for the selected drug. The doctor taps the desired dose. Optional times per day are listed and the doctor taps the desired number of times per day. Optional amount per dose (i.e. number of pills) can be listed and the doctor taps the desired amount per dose. Optional methods of administering drug can be listed and the doctor taps the desired method. Optional refill amounts can be listed and the doctor can tap the desired number of refills. Optional additional information can be listed, such as take with meals, etc. and the doctor can select the desired information by tapping. Any desired additional information can be included as desired. In this manner, no typing or writing of numbers or decimal points need be made by the doctor, which greatly reduces prescription errors. Preferably, the system reduces manual entry of numbers and words by the user to avoid mistakes.

The EHR system 100 lists all the treatment(s) related to the selected impression in block 222. Each treatment can have a code. The list in block 222 also contains the quality measures that need to be adhered for a particular impression, if any, and whether any further tests are required to comply with the quality metric. The doctor is also alerted with the patient allergies while prescribing the drugs in planning and medication block 222, or any undesired drug interactions. Required questions 203 may be presented for the doctor to answer.

In block 224, the system 100 generates a patient summary containing the selections the doctor made during the various stages of the examination. At any stage of the examination, the doctor can go back to the previous step and change the selection. The doctor can also add comments, if needed in the patient summary.

In block 226, a doctor note, receipt and claim are created once the doctor verifies the patient summary. All positive and negative symptoms can be generated in the doctor note. All positive and negative findings can be generated in the doctor note. Preferably, only selection of uniform answers is used to generate the doctor note and no written text entered by the doctor is used to generate the doctor note. In this manner, the procedure for generating all doctor notes and confirming codes is uniform among all EHR files.

The receipt contains information such as charge for the consultation, co-pay, the mode of payment, etc. The doctor needn't keep track of the procedure codes as the codes are automatically selected based on the plan and medication selected by the doctor.

A claim can then be directly send to the insurance provider 160 for claim processing. The patient's data is stored in a patient database residing on the main server 150. The doctor can access all the patient information in a dashboard view display on the user interface device 120. Once the doctor completes examination of the patient, the patient database is updated with the new examination results.

For a follow up visit, the doctor can re-examine the patient on the confirmed diagnosis. The system 100 prompts the doctor to close the patient record if the patient is cured or continue examination if the patient has not yet recovered.

The doctor can also be provided with critical information on the user display device 120, such as the patient's past medical/surgical history, social history and the family history for diagnosis that are stored in the patients record database. Past medical/surgical history can include information such as major illnesses, any previous surgery/operations, any current ongoing illness etc. The patient's social history can indicate living arrangements, occupation, marital status, drug use, etc. The patient's family history can include information about diseases or disorders from which the direct blood relatives of the patient have suffered.

Figure 3A:
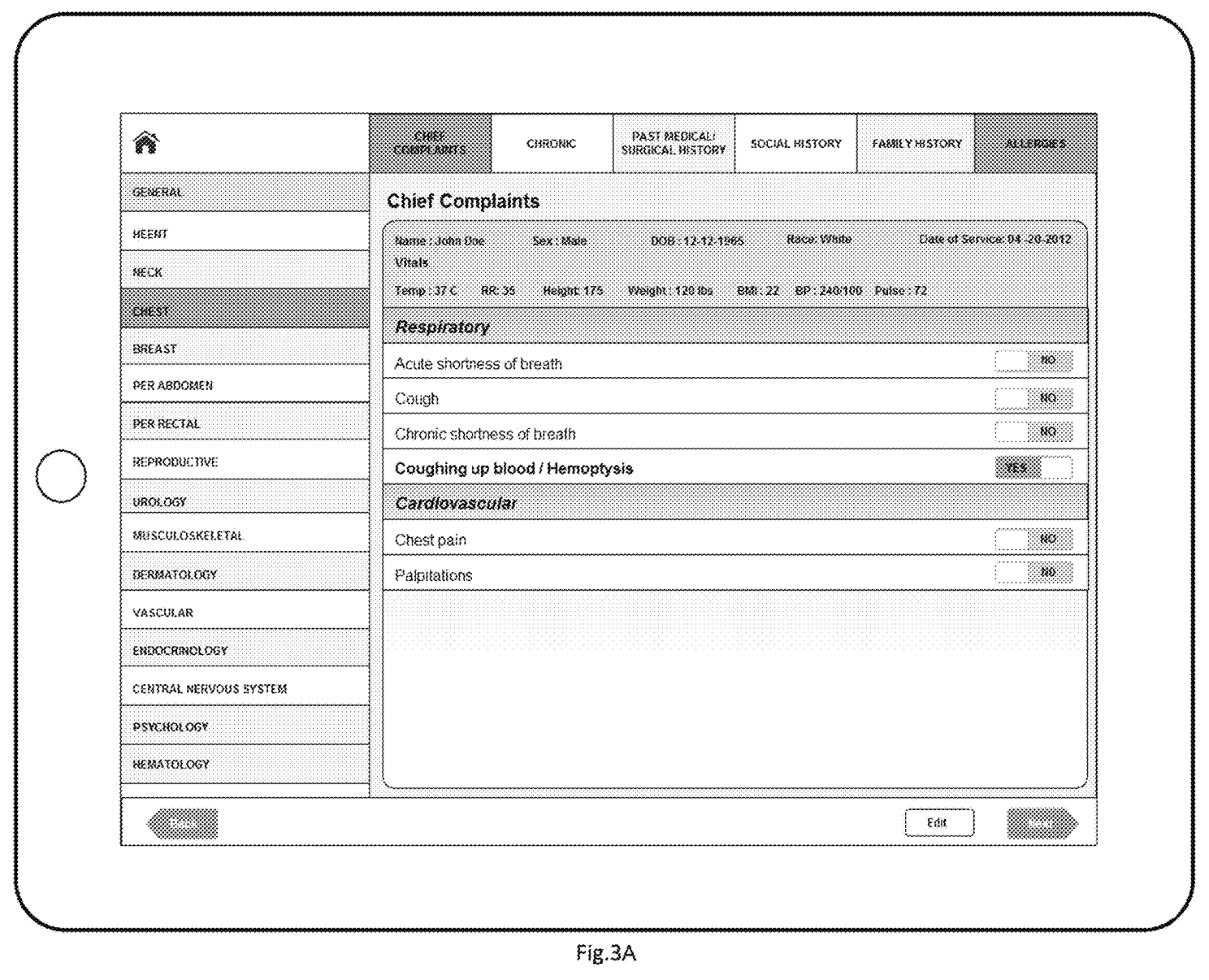
Figure 3A1:
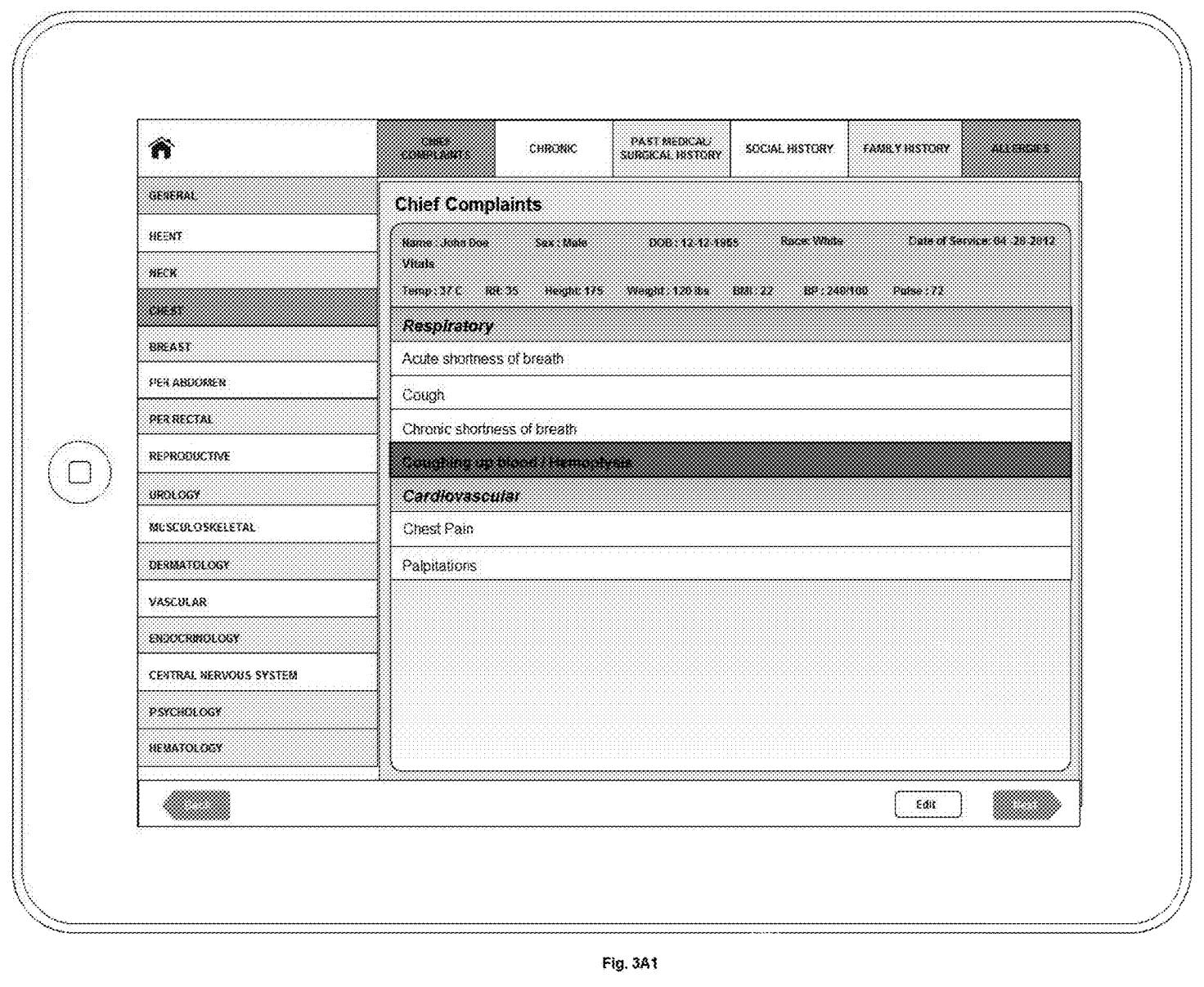
Figure 3B:
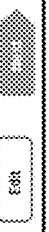
Figure 3C:
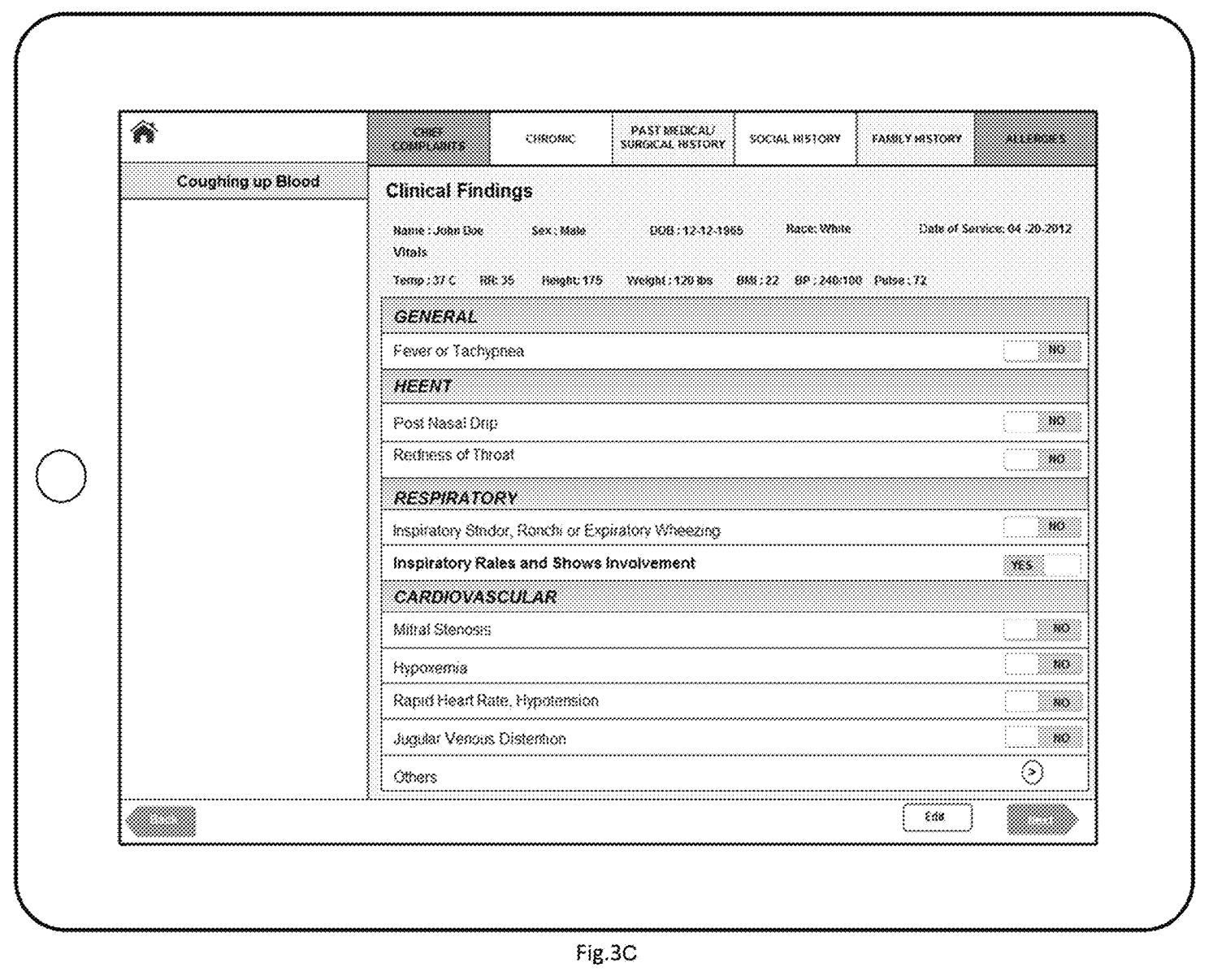
Figure 3C1:
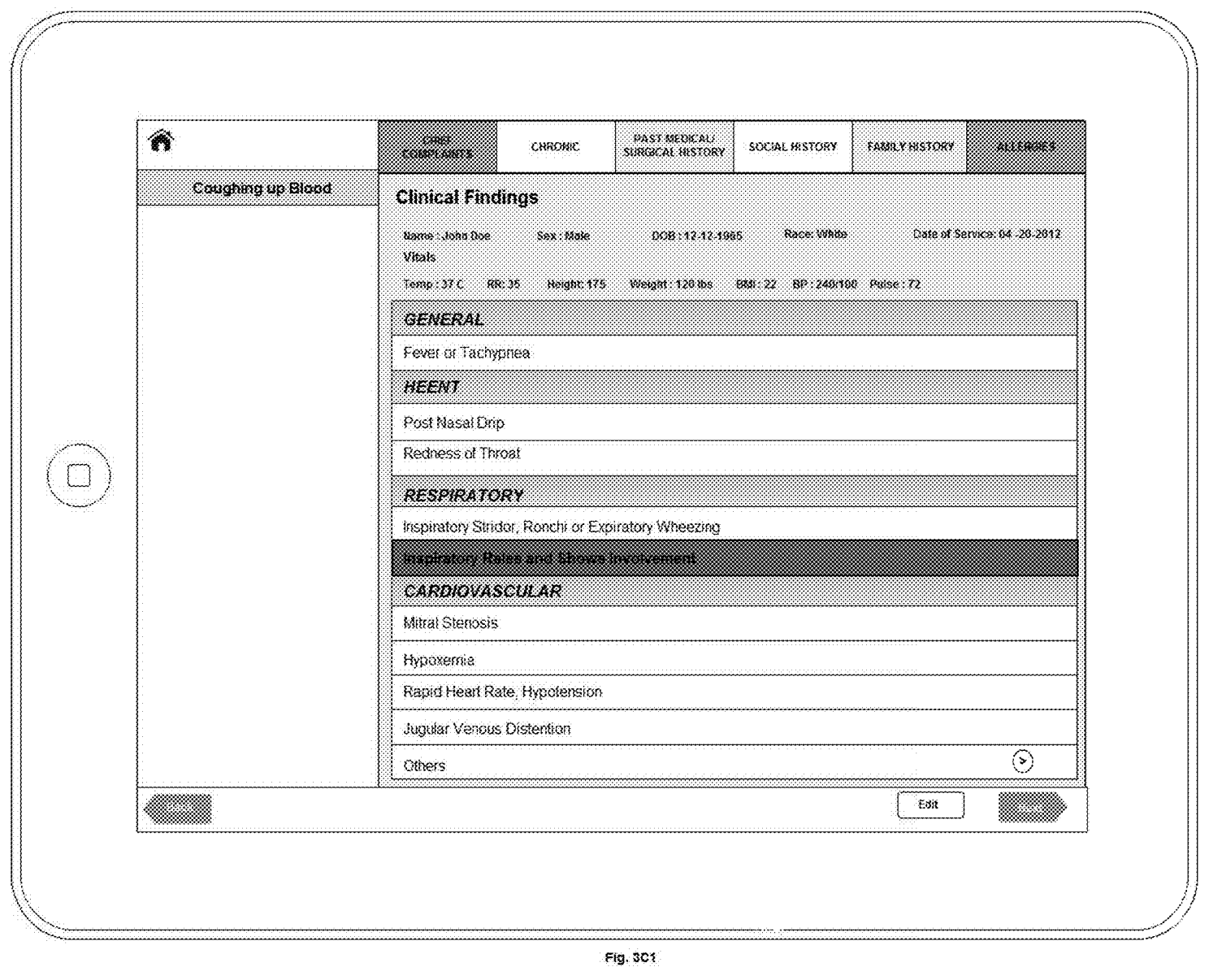
Figure 3D:
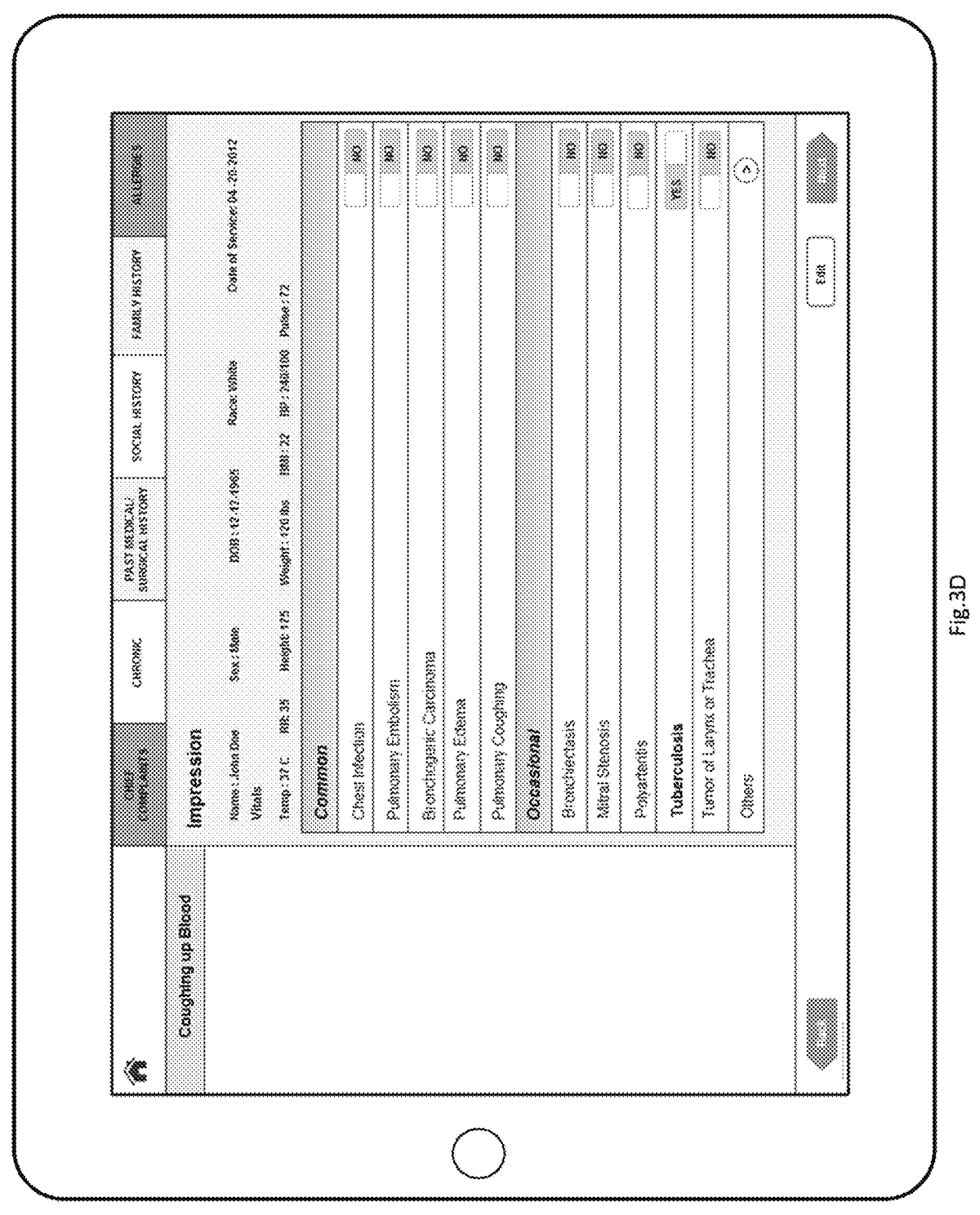
Figure 3D1:
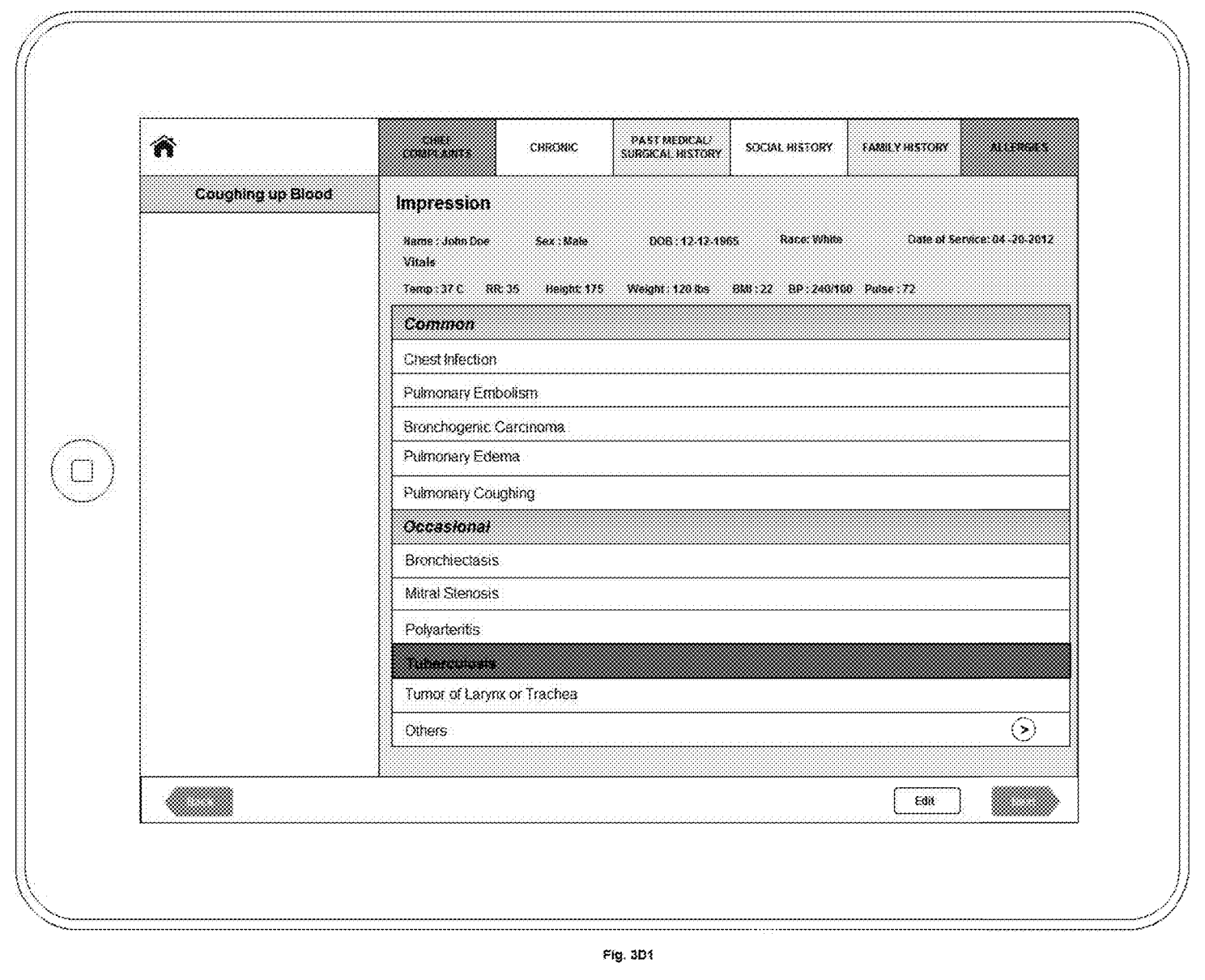
Figure 3E:
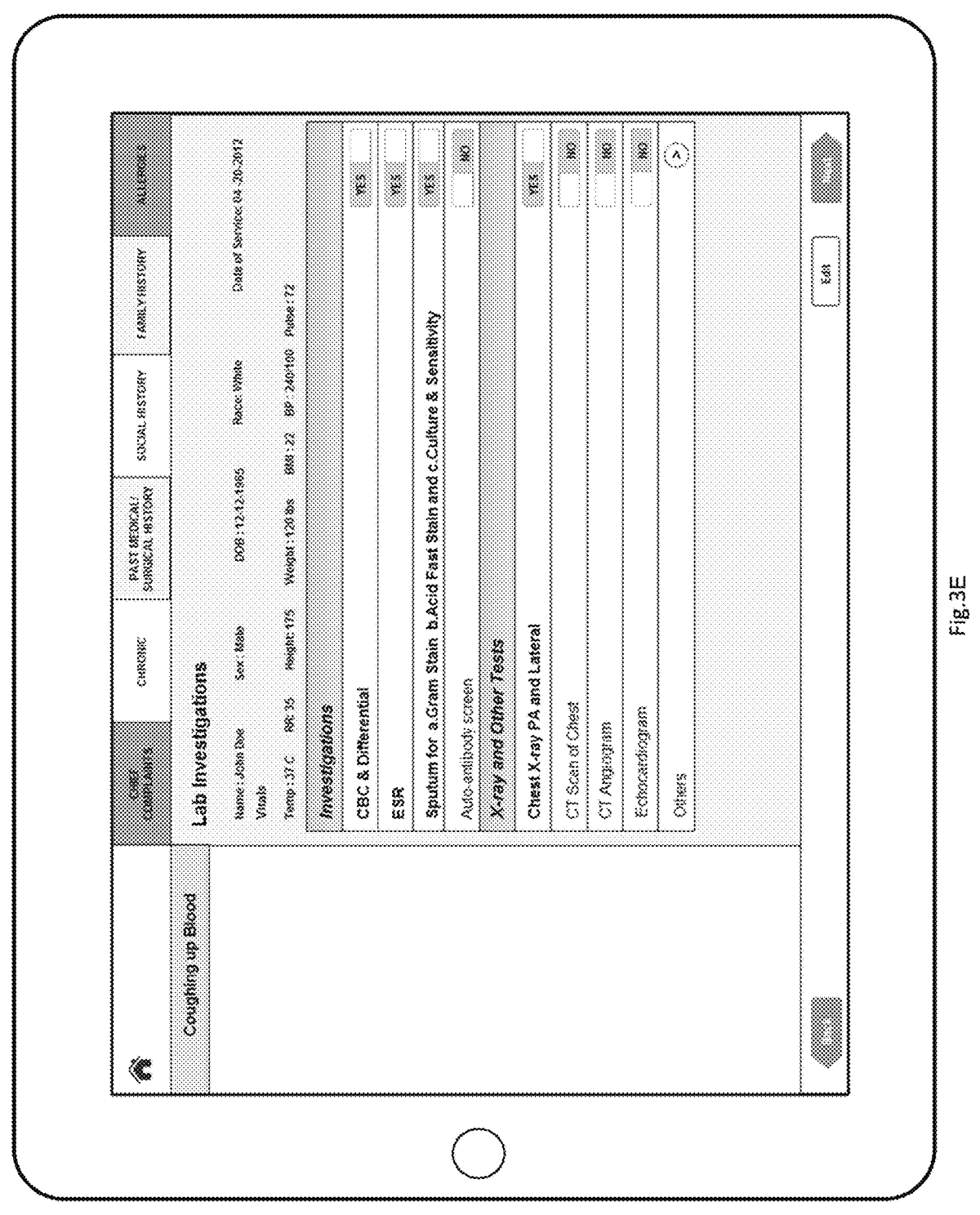
Figure 3E1:
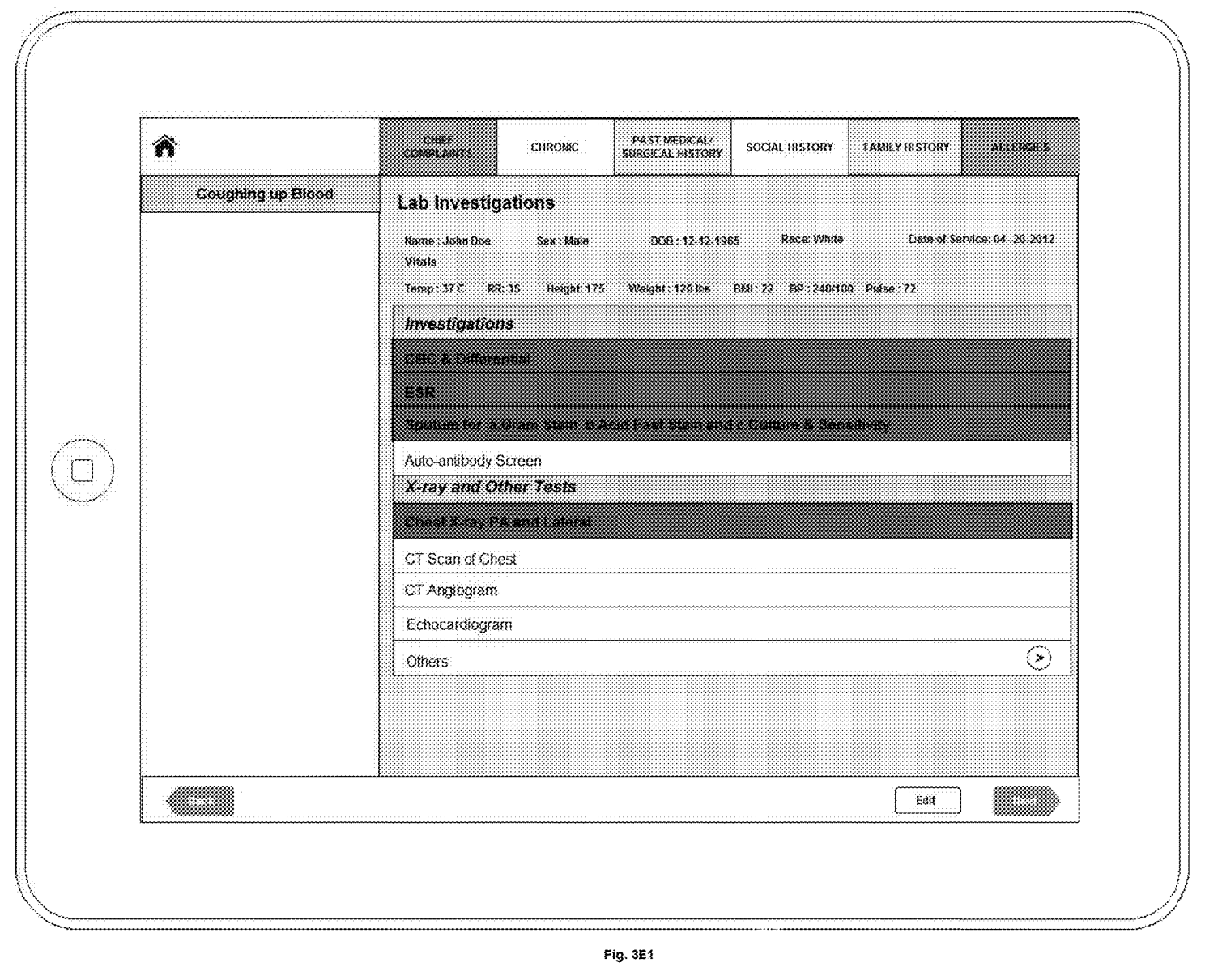
Figure 3F:
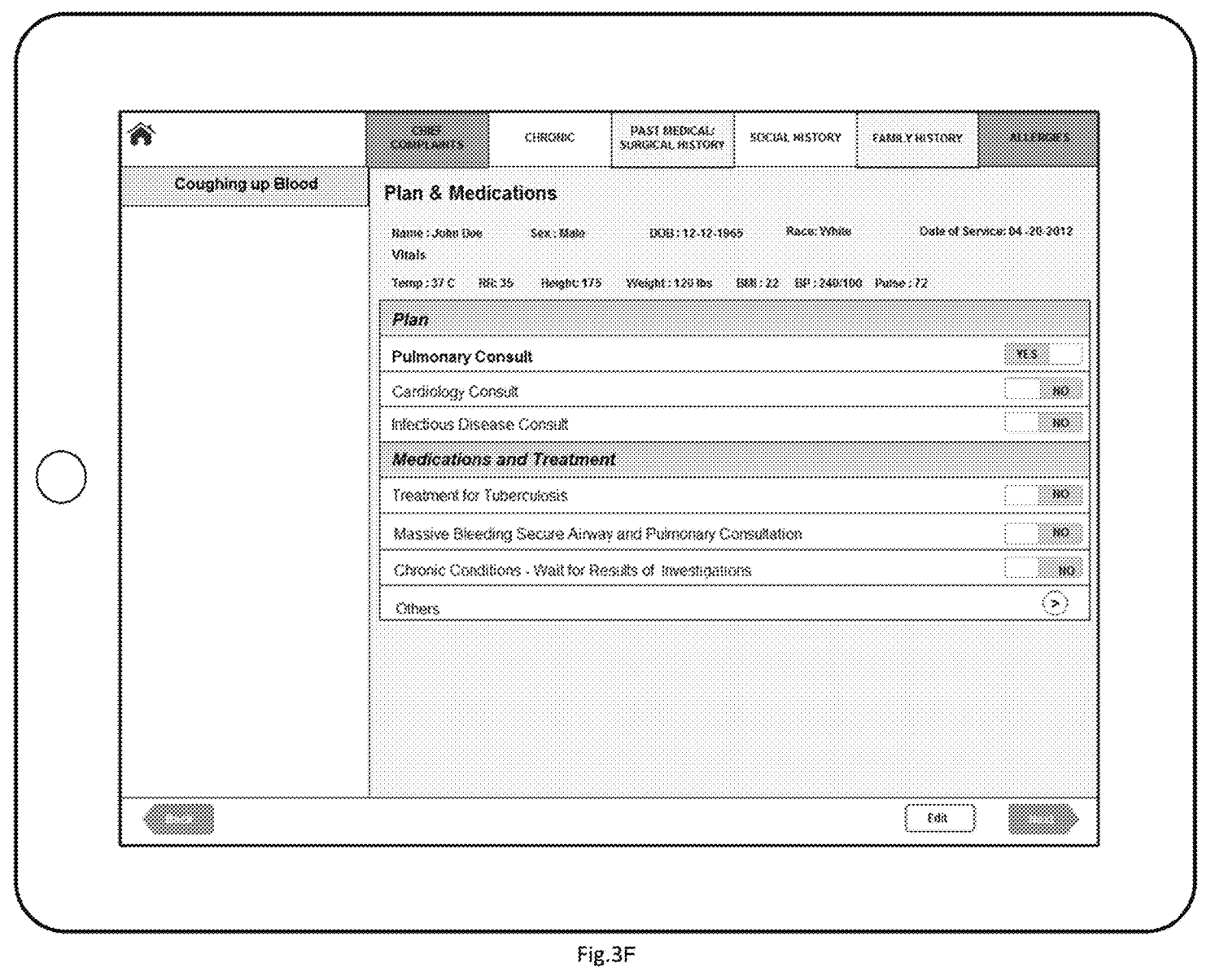
Figure 3F1:
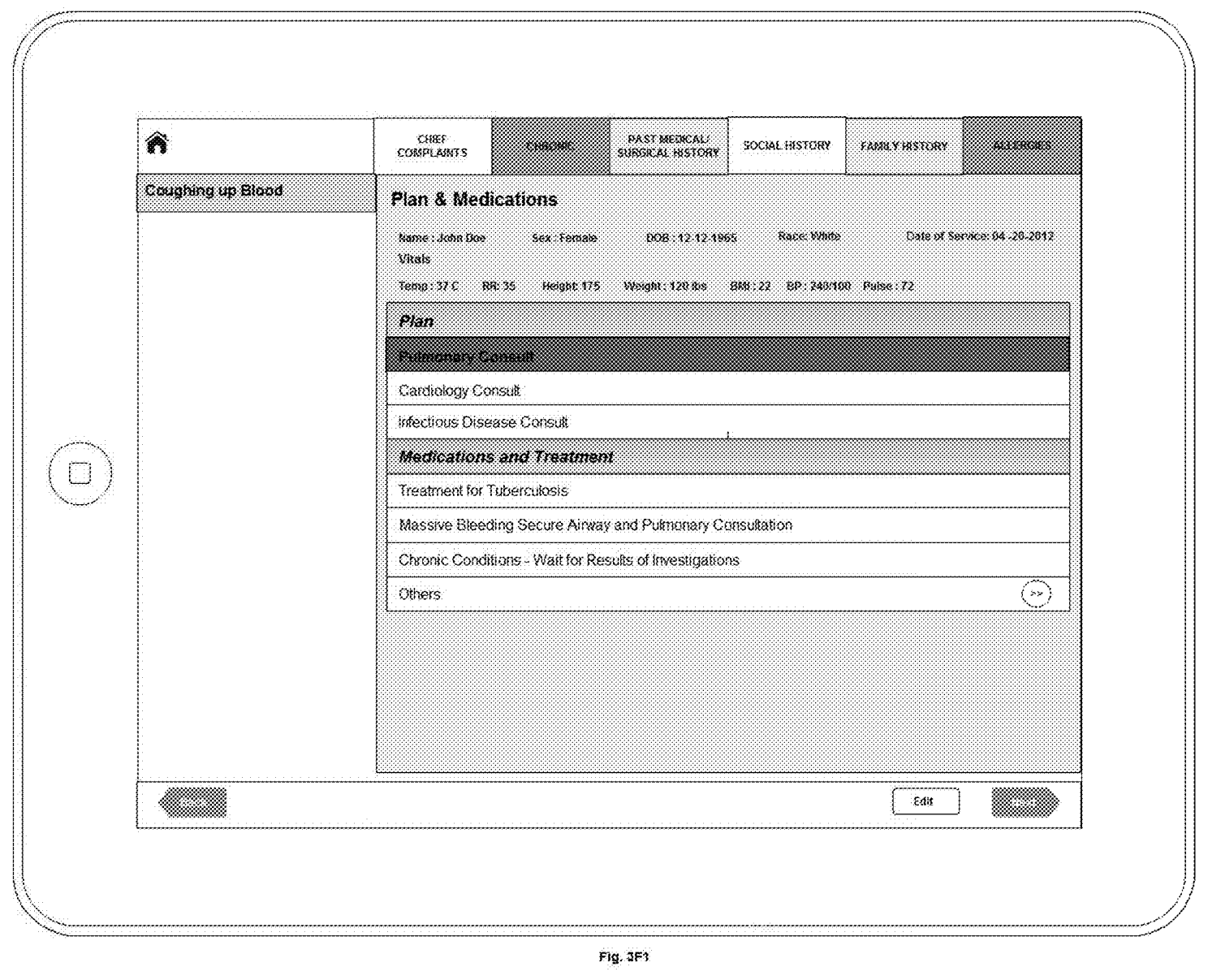
Figure 3H:
FIG. 3H illustrates an exemplary graphical user interface view of a doctor's note.
Figure 31:
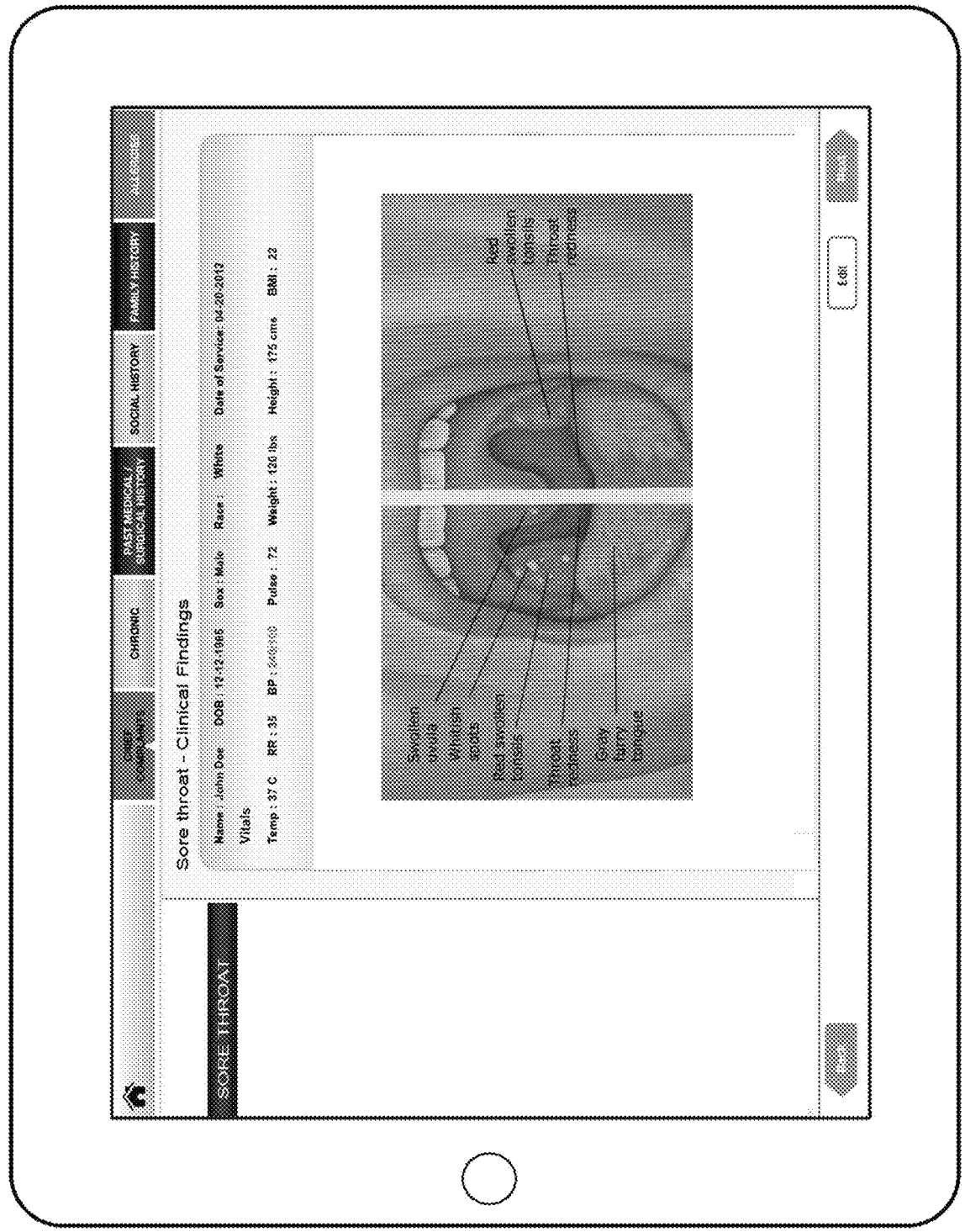

Different colors can be used to categorize any desired groups of information displayed on the doctor note. FIG. 3H shows an example of the coloring feature. The system 100 assigns a color to a particular chronic medical condition (confirmed diagnosis) and all the related information is assigned the same color. For example, in a doctor's note, all information related to diabetes mellitus can be colored green (text in solid box) and those of hyperlipidemia (cholesterol) are colored red (text in dotted box).

As shown in FIG. 3I, the list of findings can also be represented with pictures of the medical condition (confirmed diagnosis) and the doctor can select the picture that best describes the medical condition (confirmed diagnosis). When the relevant picture describing the medical condition (confirmed diagnosis) is selected, the system 100 suggests the associated impression(s) and automatically generates a text description for the findings in the doctor note. The pictures are mapped to a symptom description in the database.

Figure 7A:
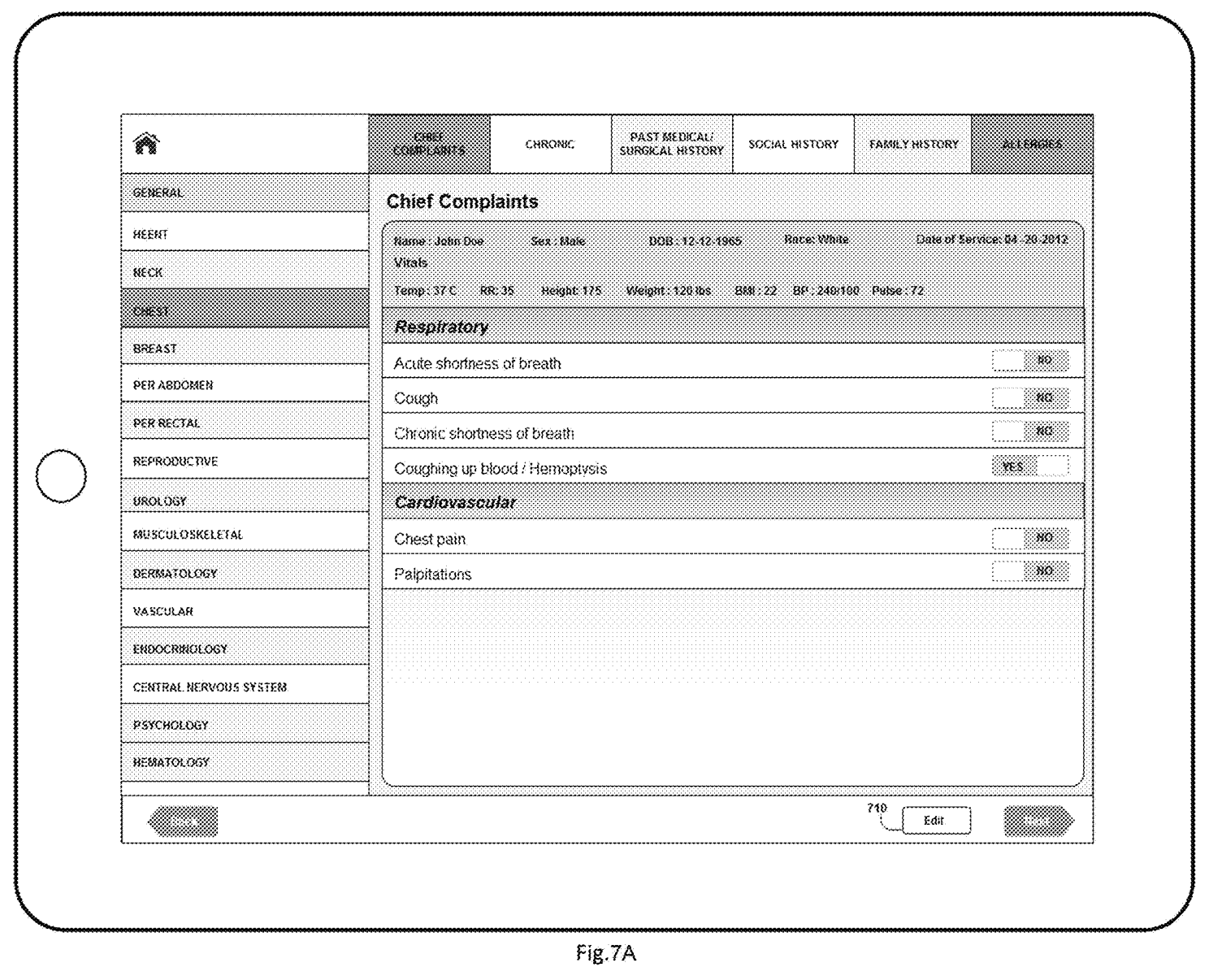
Figure 7B:
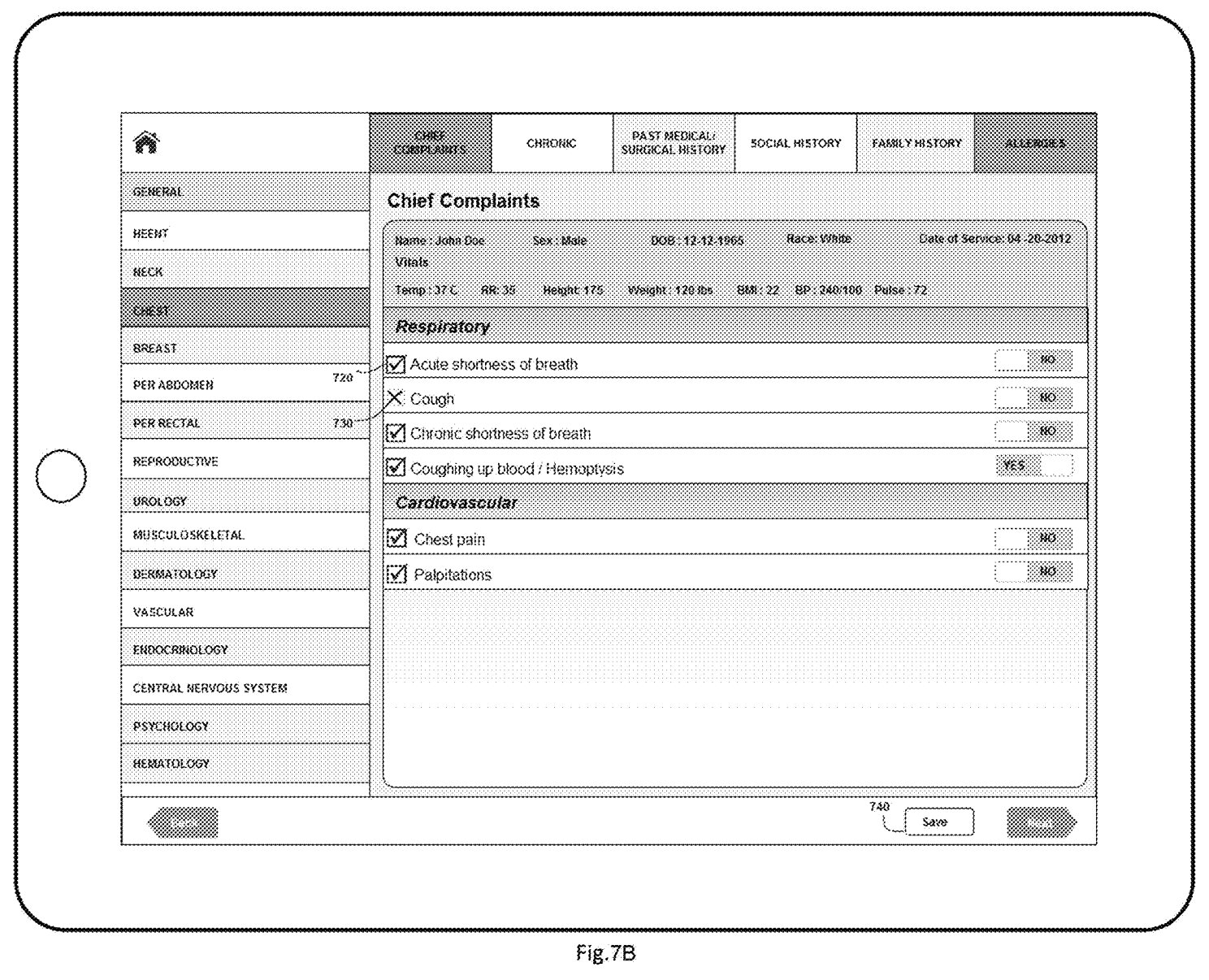

As shown in FIGS. 7A-7B, preferably, the system 100 has an activate and deactivate option. The system 100 can be configured so that each doctor can have a personal profile. The doctor can select any desired feature of the system 100 and can customize the information displayed. FIG. 7A, shows an edit button 710 in the Chief Complaints Screen. The doctor can go to edit button 710 and deactivate the options the doctor believes are irrelevant or rare for the doctor's practice. As shown in FIG. 7B, the doctor removes "Chronic Shortness of Breath" from the list by crossing the checkbox 730. The doctor ensures that all the options the doctor wants to be activated are remained checked as in checkbox 720. The action can be saved by clicking the save button 740.

As another example, if the doctor desires specific drugs to treat a patient condition (confirmed diagnosis), only the doctor's desired drugs will be displayed on the user interface device 120 in the patient's treatment plan when the doctor's profile is edited. When the doctor performs the edit option, all possible drugs used to treat the patient's condition (confirmed diagnosis) will be displayed on the user interface device 120 and the doctor can deactivate the undesired drugs. As another example, if the patient has multiple chronic conditions (confirmed diagnosis), the doctor can edit the patient's record so that the patient's record only shows information relating to a specific chronic medical condition (confirmed diagnosis) the doctor is examining at that time on the user interface device 120. When activated, all of the patient's information is displayed on the user interface device 120. A further example is if questions are being repeated by the system that the doctor desires to ignore, the undesired options can be removed during, and when activated the questions will be present. However, the doctor cannot ignore required questions 203.

The system 100 preferably includes a location device to determine the location of the patient or user interface device. The location device is preferably a GPS system present in the user interface device to determine the location of the user interface device 120. The main server 150 can contain location based information including, for example, location based impressions, symptoms, drugs, treatments, insurance carriers, or any other desired location based information. The user interface device 120 having a GPS can display the location based information.

To enhance the usability of the software, the checklist displayed is preferably minimal and most relevant to the patient under examination. The system can prioritize the list based on age, sex, time of the year, or any other desired information. Geographical or 'locational' factors can influence the outcome while examining a patient. The system can also provide location based clinical decision support. The system can prioritize the check list based on the most common disease/condition (diagnosis) based on the GPS location. The system can display the prioritized data on top of the check list and brings down the rare cases. This prioritization helps the doctor in easily selecting the required information and saves valuable time.

For example: A disease X is common to a particular region Y. A patient comes to the clinic with chief complaints leading to X. Since the doctor is examining the patient at Y, the system automatically reorders the impression list. X comes on top of the list allowing the doctor to select X as a probable diagnosis.

Chronic Flow

FIG. 2B is a flow diagram illustrating the method 240 performed by system 100 illustrated in FIG. 1. The method 240 shows the flow of the patient examination or diagnosis for a chronic condition (confirmed diagnosis) for an existing patient.

Figure 4A:
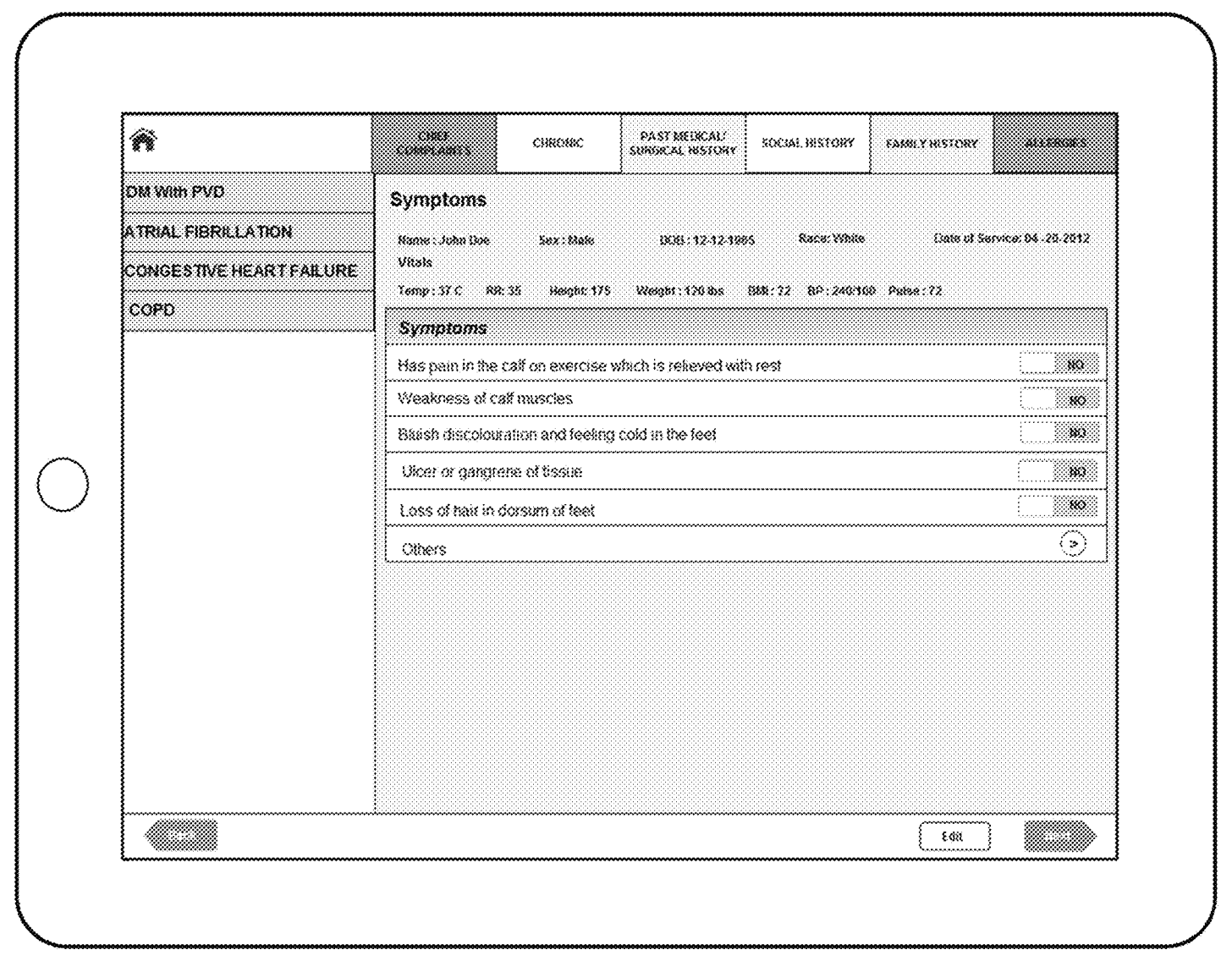
Figure 4B:
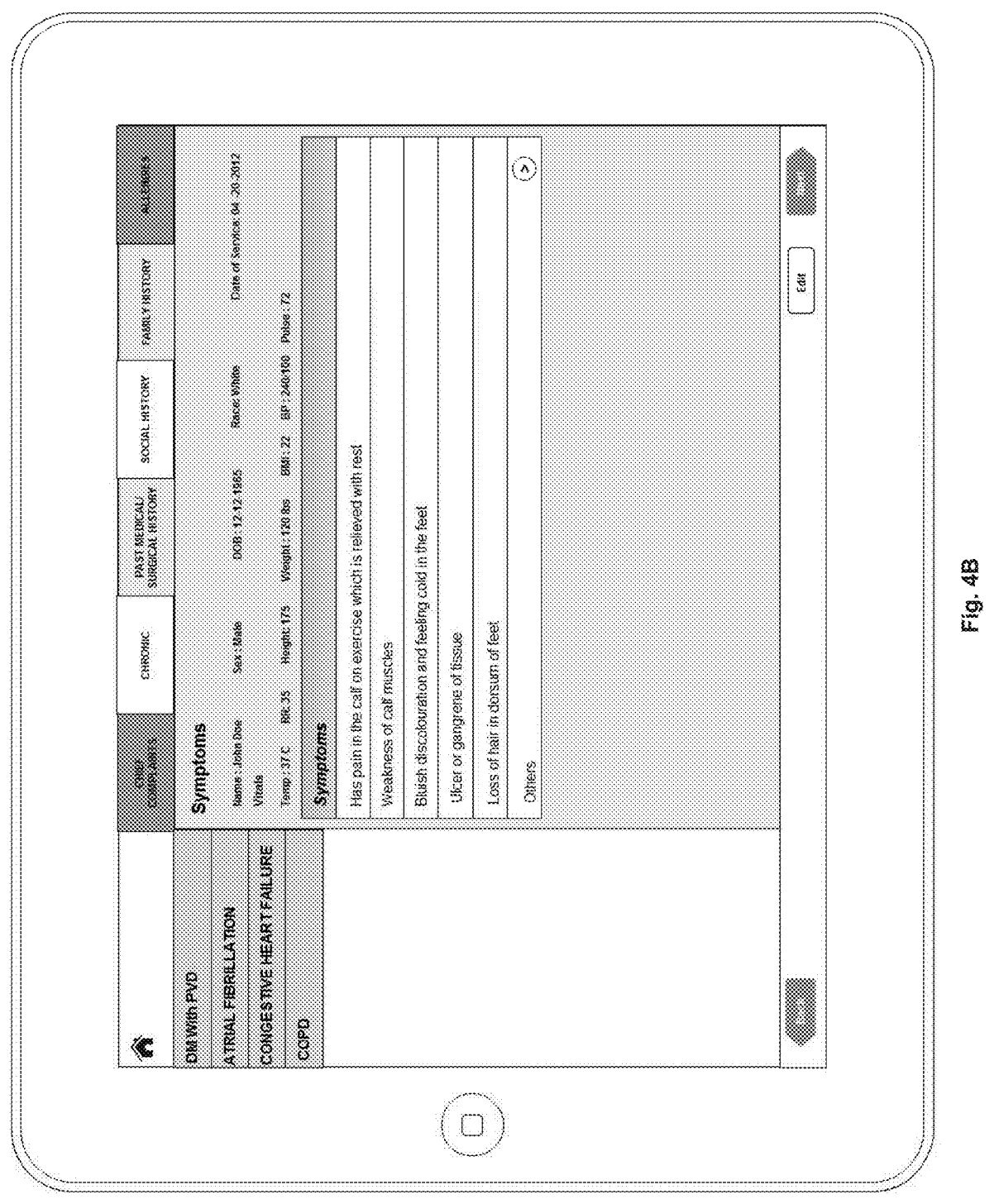

The system 100 displays all the chronic conditions (confirmed diagnosis) of the patient as shown in FIGS. 4A and 4B. The doctor selects from a list the chronic conditions (confirmed diagnosis), which can be in form of required questions 203, to be reviewed in block 242. The doctor then analyzes the lab results in block 244 and continues the examination. The doctor then updates the symptoms in block 246 and findings in block 248 if any changes are found, such as by answering the required questions 203. The system 100, prompts the doctor to change the impression for the patient's condition (confirmed diagnosis) in block 250. In block 252, the system 100 prompts the doctor to select lab investigations to analyze the severity of the chronic condition (confirmed diagnosis), which can be in the form of required questions 203, and the doctor updates the Plan and Medication accordingly in block 254, such as by answering the required questions 203. The medical alerts in block 253 provide notification during the different stages of examination. The patient summary in block 256 displays the selection made (answers to required questions 203) by the doctor and once the selections are confirmed a doctor note and receipt is generated in block 258. FIG. 4A illustrates the use of yes/no tabs (required questions) for the user to input information to the system and FIG. 4B illustrates the use of highlighting/no-highlighting for the user to input information to the system.

Security can be incorporated to ensure that the answers provided are secure.

There can be a history of past codes and answers to required questions maintained that can be viewed.

EXAMPLES OF APPLYING THE EHR SYSTEM 100 TO SPECIFIC PATIENT PROBLEMS

Example 1

As an example, consider a 47 year old male patient complaining of "coughing up blood" as the chief complaint. The patient comes into the clinic and presents the chief complaint to the nurse. The nurse measures the vitals and enters the information into the system 100 using the user interface device 120. The nurse then selects "coughing up blood" from the chief complaints screen on the user interface device 120. A screenshot shown on the display of the user interface device 120 illustrating the chief complaints pertaining to the body system "chest" is provided in FIG. 3A.

The Doctor navigates to the symptoms screen and the system 100 presents a list of causes related to coughing up blood, which is retrieved from the clinical decision support database. The list is displayed as a checklist for assisting the doctor in recording all the necessary information in each step. The checklist is sorted from most likely to least likely based on age, sex, medical and surgical history, etc. If the system does not show the desired item on the check list, the doctor can retrieve additional items from the clinical decision support database. If the doctor still fails to find the item, the doctor can either type or speak the information and have it appear in the list.

The first step in the examination of the patient can be to obtain a complete history and findings. In this patient, the doctor enquires about any additional symptoms present along with coughing up blood, and other information, referred to as findings.

The patient replies that:

"He has been exposed to someone with tuberculosis; Has travelled abroad to India within 6 months; and Has weight loss."

The doctor enters the findings. A screenshot shown on the display of the user interface device 120 illustrating the symptoms section is provided in FIG. 3B. From this history and symptomatology, the doctor now has tuberculosis on top of his list of possible impressions.

The doctor then proceeds to examine the patient. On examination of the respiratory system, he notes "inspiratory rales", a finding consistent with a diagnosis of tuberculosis. The doctor selects "inspiratory rales and shows involvement" in clinical findings. A screenshot shown on display of the user interface device 120 illustrating the clinical findings section is provided in FIG. 3C.

The Impression screen displays a list of possible impressions based on the findings and/or symptoms. Based on the findings and positive symptoms, the doctor selects Tuberculosis. A screenshot shown on the display of the user interface device 120 illustrating the impression section is provided in FIG. 3D.

The doctor now confirms or denies the impression through investigations. The lab tests required to confirm tuberculosis include CBC with differential, ESR and sputum staining for acid fast bacilli (AFB). A chest X-ray is also necessary to detect tuberculosis lesions in the lungs. The doctor selects from the investigations screen the tests needed to confirm Tuberculosis. A screenshot shown on the display of the user interface device 120 illustrating the Lab investigations is provided in FIG. 3E. The patient is referred to a lab for these tests. The doctor saves the patient chart and generates a doctor note for the first visit.

During the second visit, the doctor reopens the patient chart, lab results are entered into the patient record database, confirming the presence of acid fast bacilli in the sputum and chest X-rays showing cavitary lesions in the lungs, the doctor confirms the diagnosis of tuberculosis and arranges for a pulmonary consult. The doctor selects pulmonary consult from plan and medications. A screenshot shown on the display of the user interface device 120 illustrating the plan and medications is provided in FIG. 3F.

The screenshots shown in FIGS. 3A-3F use an embodiment in which yes/no tabs are selected by the user to input information to the system. The screenshots shown in FIGS. 3A1-3F1 use an embodiment in which highlighting/no-highlighting is selected by the user to input information to the system. For example, a positive symptom or diagnosis can be inputted as yes in one embodiment or highlighted in the other embodiment.

If the patient has a chronic condition (confirmed diagnosis), the doctor can go to the chronic section and change the plan and medication if there is any change in patient's chronic condition (confirmed diagnosis). In this example the doctor finds that the patient has diabetes and cholesterol and asks him to continue his medications.

The patient summary screen lists the selections made by the doctor in each step of the examination before generating the doctor note. The doctor can change his selections if needed by navigating back to the respective screens.

A screenshot shown on the display of the user interface device 120 illustrating the patient summary screen is provided in FIG. 3G. The patient summary screen also provides information regarding his/her chronic conditions (confirmed diagnosis) that are active. The patient summary also lists the HEDIS/PQRS quality measures, which alert physicians of necessary tests, procedures to be performed for that patient.

In FIG. 3G, the HEDIS measures lists HbA1c test and LDL screening. As a HEDIS measure, it is recommended that individuals between 18 and 75 years old with diabetes be tested for LDL-C levels at least once a year.

Once the doctor validates the information in the patient summary section he/she confirms the selections and the system generates the doctor note. The doctor note generated is in the form of a SOAP note (Subjective, Objective, Assessment and Plan) and populated based on the selections in each step of the patient examination. The doctor can also change the doctor note format to the format of his/her choice. A screenshot shown on the display of the user interface device 120 illustrating the Doctor Note Screen is provided in FIG. 3H.

The chief Complaints and the Symptoms form the Subjective part of the SOAP Note. Long description statements associated with the selected Chief Complaints and the Symptoms will be used to create the sentence for the Subjective section. The Findings constitutes the objective part. All positive and negative findings are listed in the objective section. The Assessment section contains the Impression. The final part of the SOAP note contains the Investigations, Plan and Medication.

A HCFA 1500 form (Now CMS 1500), the official standard form used by doctors when submitting bills/claims for reimbursement to insurance companies, can also be generated automatically by the system and outputted in any desired form, such as printed, displayed, copied to a computer disk, hard drive, flash memory, or other storage device in any desired electronic format.

Example 2

The patient comes to the doctor with "blood in urine" as the chief complaint. The doctor selects blood in urine as the chief complaint on the user interface. Alternatively, the doctor can select the body system associated with blood in urine, which will then display a list of possible chief complaints from which the doctor can select blood in urine.

The user interface displays the following possible symptoms associated with the selected chief complaint:

1. Burning on urination;
2. Frank blood or dark colored urine;
3. Back pain;
4. Fever and chills;
5. Painless;
6. Weight loss; and
7. Pain which travels downward.

The doctor reviews each of the listed symptoms and checks each symptom as positive (present in patient) or negative (not present in patient) in the clinical findings:

1. Fever;
2. Weight loss; and
3. Tenderness in costo-vertebral angle.

A list of possible impressions is then displayed on the user interface device:

1. Hematuria;
2. Renal Calculi;

3. Urinary tract infection;
4. Bladder tumor;
5. Kidney tumor; and
6. Trauma to kidney.

The doctor selects a possible impression and then an investigation is displayed with required labs and/or X-rays:
1. CBC;
2. Urine analysis and CTS;
3. Ultra sound of Kidney;
4. IVP; and
5. CT Scan.

The impression is confirmed or denied based on the outcome of the investigation.

A plan and medication screen is displayed for a confirmed impression, which lists the required treatment.

In an alternative embodiment, the possible diagnoses are displayed in separate columns or rows. A plurality of separate columns or rows are displayed on the same screen. During the patient review, as possible diagnoses are ruled out, the column or row with the ruled out possible diagnosis is selected and removed, and the remaining rows or columns move to replace the removed row or column on the display.

Example 3

A 60-year old white woman comes with the complaint of chest pain since one week. The blood pressure as recorded by the nurse is 130/86 mm Hg. BMI is 30.

The doctor views additional details about the patient from the history. He finds that the patient is diabetic and hypertensive for 10 and 5 years respectively. Family history is positive for hypertension in mother and elder brother and father dying of heart attack at age 62. She is on T. Glucophage (Metformin) 500 mg BD, T. Microzide (Hydrochlorthiazide) 25 mg OD and T. Tenormin (Atenolol) 50 mg OD, apart from Vitamin B supplements as shown in FIG. 8A FIG. 8A shows an active medication list 151 of the patient. The active medication list 151 displays the brand name along with the generic name, dosage, frequency, duration, start date and instructions. For changing an existing medication the doctor selects a drug from the active medication list and taps on the change button 152. The system then provides a list of alternatives for that particular drug. To discontinue a medication, the doctor taps twice 153 on the drug with a delete confirmation alert 154. To add a drug to the active medication list 151, the doctor can search the drug and use the add button 156 to include the drug.

Figure 9A:
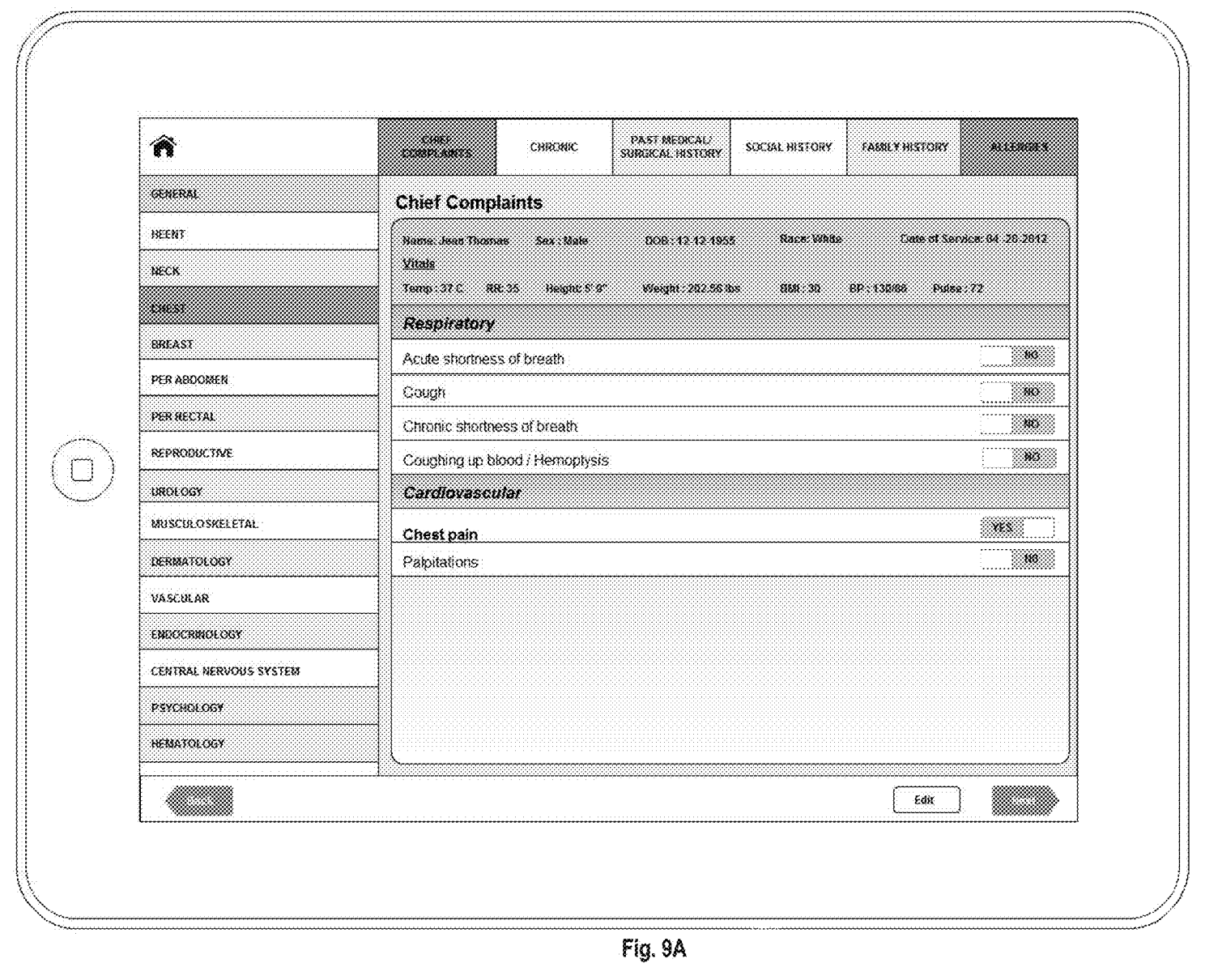

The doctor selects Chest pain from the list of Chief Complaints under CHEST section, shown in FIG. 9A.

Figure 9B:
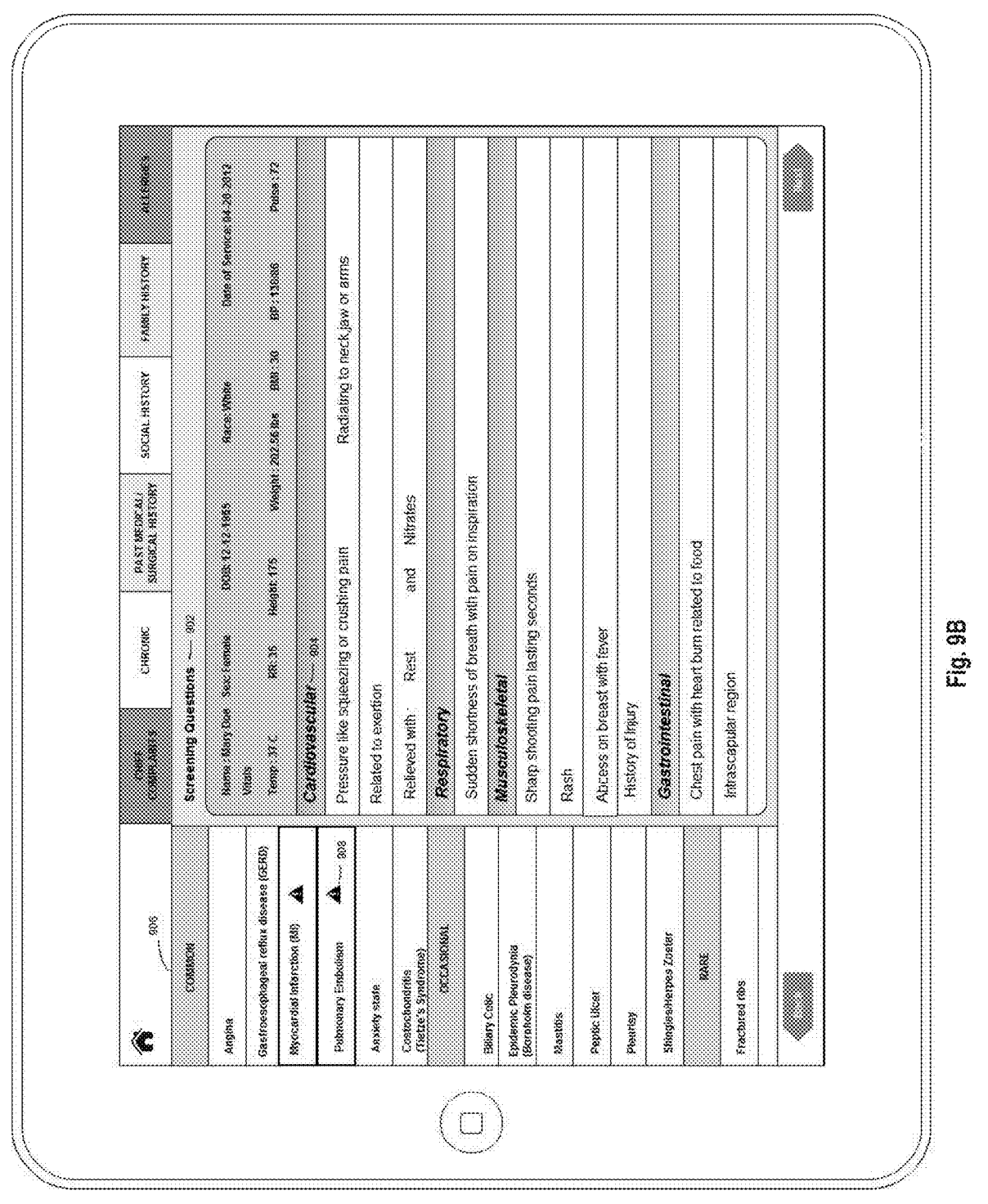

The differential diagnoses 906 for chest pain are enumerated in the left side of the screen shown in FIG. 9B and categorized as Common, Occasional and Rare. The system suggests the questions that need to be enquired with the patient so as to narrow down the possible diagnosis. The diagnosis with an alert 908 are severe conditions (confirmed diagnosis). In this example, Myocardial Infarction (heart attack) and Pulmonary Embolism (blood clot to lung) are severe possible diagnosis (conditions) and they should not be missed by the user during examination.

Figure 9C:
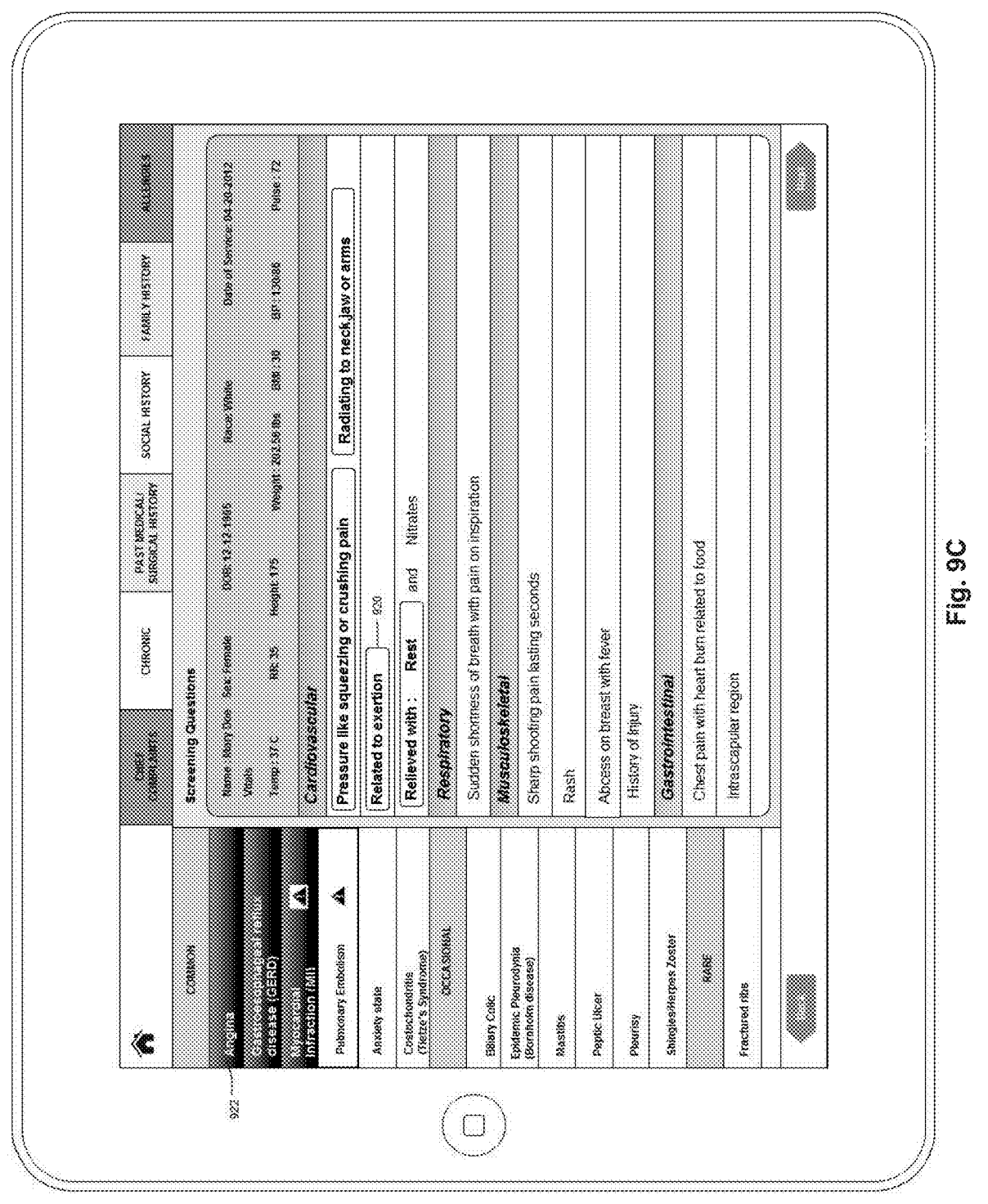

An Initial set of screening questions 902 are presented categorized into organ systems 904 based on the selected chief complaint. Based on the description provided by the patient, the doctor selects the desired values 920 from the display screen as shown in FIG. 9C. The system then automatically selects and highlights the top three or four possible diagnosis consistent with the selected values 922.

In this patient, the onset of pain is with activity (exertion). The pain dissipates with a few minutes of rest. The pain is described as "burning" and located at the center of the chest. These points are consistent with a diagnosis of Angina. In addition, she has a family history of ischemic heart disease and hypertension, history of diabetes and hypertension as well as smoking, which are all risk factors for ischemic heart disease (these points are noted in history). The user then proceeds to the rest of the screens, i.e. Symptoms, Findings, etc.

The history of "burning pain", nausea and sensation of reflux makes the user also consider GERD. The user then proceeds with the physical exam. In this case, there are no findings. The Findings section is thus left without any selection.

To confirm the diagnosis of Angina, which is the most likely diagnosis as per the history and symptoms and to rule out MI (which is life-threatening), the doctor orders EKG. In addition, complete blood count and lipid profile are ordered from the Lab investigation screen. Nitroglycerine, and Rantidine are prescribed in the first visit from the Plan and Medication screen. The doctor may meanwhile also prescribe antacids or other treatment for GERD.

FIG. 8B shows the selection of drugs during the Plan and Medication stage. The Medications 161 are organized into drug classifications 162. The doctor can view the various drugs under the classification by taping the expand button 163. While prescribing medication, the doctor orders a drug 164 by selecting from the available drug list. The dosage, frequency, route of administration and comments for the drug 164 is also entered from the options list 166. A possible drug-drug interaction with the existing medications will be alerted during selection.

The patient comes on the $3^{rd}$ day after the first visit and reports that she still gets chest pain on activity but it subsides within a few minutes when he takes nitroglycerine. The patient is able to walk pain free for an hour after that. His EKG was normal, and so are the labs except for borderline high lipids.

The doctor opens the patient medical record and presented with the lab and radiology results. The patient can be referred to a cardiologist for further work-up and optimal treatment if necessary.

Lab Results

| Complete blood count | |
|---|---|
| 1. WBC count | 8000 cells/mm3 |
| 2. Differential count | |
| Neutrophils | 56 |
| Lymphocytes | 28 |
| Monocytes | 4 |
| Eosinophils | 4 |
| Basophils | 1 |
| 3. RBC count | 4.25 |
| 4. Hematocrit | 44% |
| 5. Hemoglobin | 15 g/dl |
| 6. Platelet count | 2,20,000/mm3 |

| Lipid profile | |
|---|---|
| Total cholesterol | 220 mg/dl |
| LDL | 172 mg/dl |
| HDL | 55 mg/dl |
| Triglycerides | 150 mg/dl |

Example 4

The codes for cancer of the pancreas:
(A) Head of pancreas
(B) Body of pancreas
(C) Tail of pancreas
The normal sources to obtain this information are
1) Surgical report by the doctor during surgery.
2) Radiology reports from
   i) Ultrasound of abdomen
   ii) MRI of abdomen
   iii) Catscan of abdomen
3) Pathology report by pathologist who will identify the site of the pancreatic tumor.
Lab Results Each source must answer any required questions. Unless all of these specialties are forced to report (provide answers) on the basis of a uniform checklist of required questions in the EHR, it will not be possible to code accurately.

Similarly, since the present EHR is built up using the codes as the foundation and uniform notes (required questions) created for each code taking it through the history, examining the patient, making the diagnosis, and ordering investigations and a treatment plan covering each aspect and variations of all diseases, now greatly decreases the chances of doctors missing diagnosis.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention. Therefore, it is intended that the invention not be limited to the particular embodiments disclosed as the best mode contemplated for carrying out this invention, but that the invention will include all embodiments falling within the scope and spirit of the appended claims. In addition, the logic flows depicted in the figures do not require the particular order shown, or sequential order, to achieve desirable results.

For example, this invention has been described using the PQRS and HEDIS quality metrics for the quality metric requirements database. However, the quality metric requirements database can be based on any other desired quality metric, such as quality metrics developed by countries other than the U.S. Furthermore, while the present invention has been described in regards to internal medicine, the present invention is also applicable to any type of specialty.

I claim:

1. A method of making a patient health care record comprising;
    displaying, by a user interface device, a list of possible chief complaints;
    selecting by a user at least one chief complaint from the list on the user interface, each chief complaint being associated with a unique code; and
    displaying, by the user interface, a list of symptoms associated with the selected chief complaint in the form of required questions, the required questions being associated with the unique code, the required questions can only be answered by selection so that answers to required questions are uniform, and the codes can only be confirmed or denied by answering required questions;
    displaying, by the user interface, a differential diagnosis categorizing possible diagnosis;
    identifying by the user at least one of the symptoms as positive for the patient from among the displayed symptoms list on the user interface device;
    displaying, by the user interface, a findings screen that displays a list of possible findings associated with at least one positive symptom or the chief complaint, or a combination of the chief complaint and at least one positive symptom;
    displaying, by the user interface, an impressions screen that displays a list of possible impressions based on at least one of a positive symptom or a finding;
    selecting by the user at least one possible impression on the user interface;
    displaying, by the user interface device, a list of investigations associated with the selected impression;
    confirming or denying by the user the impression on the user display device based on results of the investigation;
    optionally selecting by the user a different impression on the user interface device if the impression is denied based on the investigation;
    displaying by the user interface a plan and medication screen if the impression is confirmed that displays a treatment; and
    generating and outputting by the user interface a doctor note and invoice, wherein the user interface device sending a query related to at least one of the selected impressions to a quality metrics database to confirm that the treatment complies with the quality metric and whether additional tests are required to comply with the quality metric.

2. The method according to claim 1, further comprising selecting, by the user, a category of diagnosis, wherein only the symptoms associated with the selected category of diagnosis are displayed by the user interface.

3. The method according to claim 1, further comprising displaying screening questions by the user interface, selecting by the user, answers to the screening questions, and displaying, by the user interface, a category of diagnosis.

4. The method according to claim 1, wherein the quality metric comprises Physician Quality Reporting System (PQRS) or Healthcare Effectiveness Data and Information Set (HEDIS) requirements.

5. The method according to claim 4, further comprising updating the PQRS/HEDIS requirements database in a requirements database connected to a network, and the user interface device being connected to the network.

6. The method according to claim 4, further comprising generating an invoice including required supporting notes to comply with PQRS/HEDIS requirements for payment and forwarding the invoice to an insurance carrier.

7. The method according to claim 1, further comprising displaying by the user interface a representative human body on the user display having selectable body systems, selecting a body system associated with the chief complaint by the user on the user interface, and displaying by the user interface the list of chief complaints associated with the selected body system.

8. The method according to claim 1, further comprising determining by the user interface device whether any PQRS/HEDIS procedures are required for each impression, and the user interface device displaying any required PQRS/HEDIS procedures for each impression.

9. The method according to claim 1, further comprising generating a patient visit form providing a summary of a current office visit or a patient health summary report providing a summary of the patient's existing confirmed diagnosis, medications and vitals by the user interface.

10. The method according to claim 1, wherein the user interface device comprises a touch screen, the method further comprising selecting at least one of a chief complaint, a symptom, a finding, or an impression using the touch screen during an examination of the patient.

11. The method according to claim 1, wherein the user interface device further comprises a camera, the method further comprising taking a picture or video of a patient symptom or confirmed diagnosis and storing the picture in a patient records database stored on a data storage unit.

12. The method according to claim 1, further comprising the user interface device displaying a medical alert in response to at least one of a positive symptom, a finding, or an impression.

13. The method according to claim 1, further comprising using a location device to determine the location of the user interface device and modify the information displayed on the user interface based on the location of the user interface device.

14. The method according to claim 1, further comprising displaying only user desired information on the user interface device by activating or deactivating the elements in the list.

15. An apparatus for making a patient health care record and invoice comprising:
 a cloud based server connected to a network, the cloud based server being in communication with or comprising at least one non-volatile memory, a database stored in the non-volatile memory, the database comprising a patient records database;
 a user interface device in communication with the cloud based server via the network; and
 a chief complaint software module for displaying a list of chief complaints, wherein the chief complaint software module is stored in the non-volatile memory, each chief complaint having a code, and the chief complaint software module allows a user to select at least one chief complaint of a patient from among the list of chief complaints in the form of required questions, the required questions being associated with the code;
 the database comprising a clinical decision support database, and a quality metric requirements database;
 a symptoms software module for displaying a list of symptoms associated with a selected chief complaint, wherein the symptoms software module is stored in the non-volatile memory, and the symptom software module allows a user to optionally identify each symptom as positive via the user interface device;
 a differential diagnosis software module for categorizing possible diagnosis;
 a findings software module for displaying a list of possible findings associated with at least one positive symptom or the chief complaint, or a combination of the chief complaint and at least positive symptom, wherein the findings software module is stored in the non-volatile memory;
 an impressions software module for displaying a list of possible impressions based on at least one of a positive symptom or a finding, wherein the impressions software module is stored on the non-volatile memory, and the impressions software module allows a user to select a possible impression via the user interface device;
 an investigations software module for displaying a list of investigations associated with a possible impression, wherein the investigations software module is stored on the non-volatile memory, and wherein the impressions software module allows a user to confirm or deny a possible impression based on an outcome of an investigation;
 a plan and medication module for displaying a treatment associated with a confirmed impression, wherein the plan and medication module is stored on the non-volatile memory;
 a query software module for sending a query to the at least one database to retrieve information from the database, the query software constructed for sending a query to the quality metric requirements database including regarding requirements in connection with the at least one selected impression via the user interface device to confirm that the treatment complies with the quality metric and whether additional tests are required to comply with the quality metrics, wherein the query software module is stored on non-volatile memory; and
 an invoice module for creating a patient health care record and, if an impression is confirmed, an invoice, wherein the invoice and patient health care record are saved to the patient records database.

16. The apparatus according to claim 15, wherein the quality metric comprises Physician Quality Reporting System (PQRS) or Healthcare Effectiveness Data and information Set (HEDIS) requirements.

17. The apparatus according to claim 15, wherein the chief complaint software module is further configured to display representative human body on the user display having selectable body systems, that allows a user to select a body system associated with the chief complaint on the user interface, and the chief complaint software module displaying the list of chief complaints associated with the selected body system.

18. The apparatus according to claim 15, further comprising a medical alert module for displaying a medical alert on the user interface device in response to at least one of a positive symptom, a finding or an impression.

19. The apparatus according to claim 15, wherein the user interface comprises a GPS location system and the system is constructed to modify information displayed on the user interface device based on the GPS location of the user interface device.

20. A computer readable medium storing instructions executable by a computing system including at least one cloud-based server and user interface device, wherein execution of the instructions implements a method comprising
 displaying, by a user interface device, a list of possible chief complaints;
 selecting by a user at least one chief complaint from the list on the user interface, each chief complaint being associated with a unique code; and
 displaying, by the user interface, a list of symptoms associated with the selected chief complaint in the form of required questions, the required questions being associated with the unique code, the required questions can only be answered by selection so that answers to required questions are uniform, and the codes can only be confirmed or denied by answering required questions;
 displaying, by the user interface, a differential diagnosis categorizing possible diagnosis;
 identifying by the user at least one of the symptoms as positive for the patient from among the displayed symptoms list on the user interface device;

displaying, by the user interface, a findings screen that displays a list of possible findings associated with at least one positive symptom or the chief complaint, or a combination of the chief complaint and at least one positive symptom;

displaying, by the user interface, an impressions screen that displays a list of possible impressions based on at least one of a positive symptom or a finding;

selecting by the user at least one possible impression on the user interface;

displaying, by the user interface device, a list of investigations associated with the selected impression;

confirming or denying by the user the impression on the user display device based on results of the investigation;

optionally selecting by the user a different impression on the user interface device if the impression is denied based on the investigation;

displaying by the user interface a plan and medication screen if the impression is confirmed that displays a treatment; and generating and outputting by the user interface a doctor note and invoice, wherein the user interface device sending a query related to at least one of the selected impressions to a quality metrics database to confirm that the treatment complies with the quality metric and whether additional tests are required to comply with the quality metric.

* * * * *